United States Patent
Coenen et al.

(10) Patent No.: US 10,596,047 B2
(45) Date of Patent: Mar. 24, 2020

(54) ELASTICATED MATERIALS WITH DIRECTIONAL STRETCH PROPERTIES

(71) Applicant: Kimberly-Clark Worldwide, Inc., Neenah, WI (US)

(72) Inventors: Joseph D. Coenen, Kaukauna, WI (US); Ross T. Kaufman, Appleton, WI (US); Kelly D. Farmer, Neenah, WI (US); Jerry L. Hameister, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 213 days.

(21) Appl. No.: 15/751,641

(22) PCT Filed: Apr. 27, 2017

(86) PCT No.: PCT/US2017/029861
§ 371 (c)(1),
(2) Date: Feb. 9, 2018

(87) PCT Pub. No.: WO2018/160208
PCT Pub. Date: Sep. 7, 2018

(65) Prior Publication Data
US 2019/0374398 A1 Dec. 12, 2019

Related U.S. Application Data
(60) Provisional application No. 62/464,640, filed on Feb. 28, 2017.

(51) Int. Cl.
*A61F 13/49* (2006.01)
*A61F 13/496* (2006.01)
(52) U.S. Cl.
CPC ...... *A61F 13/496* (2013.01); *A61F 13/49015* (2013.01); *A61F 2013/49026* (2013.01)

(58) Field of Classification Search
CPC .............. A61F 13/49012; A61F 13/496; A61F 2013/49025; A61F 2013/49026; A61F 2013/51083; A61F 2013/51085
See application file for complete search history.

(56) References Cited

U.S. PATENT DOCUMENTS 6,291,039 B1    9/2001   Combe et al.
7,217,261 B2 *   5/2007   Otsubo ............. A61F 13/49011
                                                      604/361

(Continued)

FOREIGN PATENT DOCUMENTS

WO    WO 2008/041639 A1    4/2008

OTHER PUBLICATIONS

Co-pending U.S. Appl. No. 15/751,565, filed Feb. 9, 2018, by Coenen et al. for "Elasticated Materials with Directional Stretch Properties.".

*Primary Examiner* — Catharine L Anderson
(74) *Attorney, Agent, or Firm* — Kimberly-Clark Worldwide, Inc.

(57) ABSTRACT

Elasticated materials and absorbent articles comprising elasticated materials are disclosed. In an embodiment, an elasticated material may comprise a first layer bonded to a second layer by first bonds and second bonds. A plurality of elastomeric strands may extend between the first layer and the second layer. A first bond and a second bond are disposed on opposite sides of a first strand and are separated by a longitudinal distance less than an un-tensioned diameter of the first strand, and a third bond and a fourth bond are disposed on opposite sides of a second strand and are separated by a longitudinal distance less than an un-tensioned diameter of the second strand. The first bond forms a first angle with respect to the first strand, the third bond (Continued)

forms a second angle with respect to the second strand, and the first angle is different than the second angle.

20 Claims, 19 Drawing Sheets

(56) References Cited

U.S. PATENT DOCUMENTS

| | | |
|---|---|---|
| 7,582,348 B2 | 9/2009 | Ando et al. |
| 8,647,319 B2 | 2/2014 | Een et al. |
| 2005/0095942 A1 | 5/2005 | Mueller et al. |
| 2013/0324956 A1 | 12/2013 | Zink et al. |
| 2014/0221956 A1 | 8/2014 | Martynus et al. |
| 2015/0328056 A1 | 11/2015 | Een et al. |
| 2016/0159062 A1 | 6/2016 | Sablone |
| 2016/0228305 A1 | 8/2016 | Gualtieri et al. |
| 2016/0288407 A1 | 10/2016 | Ehlert et al. |
| 2016/0324694 A1* | 11/2016 | Umebayashi ..... A61F 13/49012 |
| 2016/0331600 A1 | 11/2016 | Polidori et al. |
| 2017/0000660 A1 | 1/2017 | Wade et al. |
| 2017/0231837 A1* | 8/2017 | Tashiro ............. A61F 13/49011 604/385.3 |
| 2017/0231839 A1* | 8/2017 | Tashiro ................ A61F 13/515 604/385.3 |

* cited by examiner

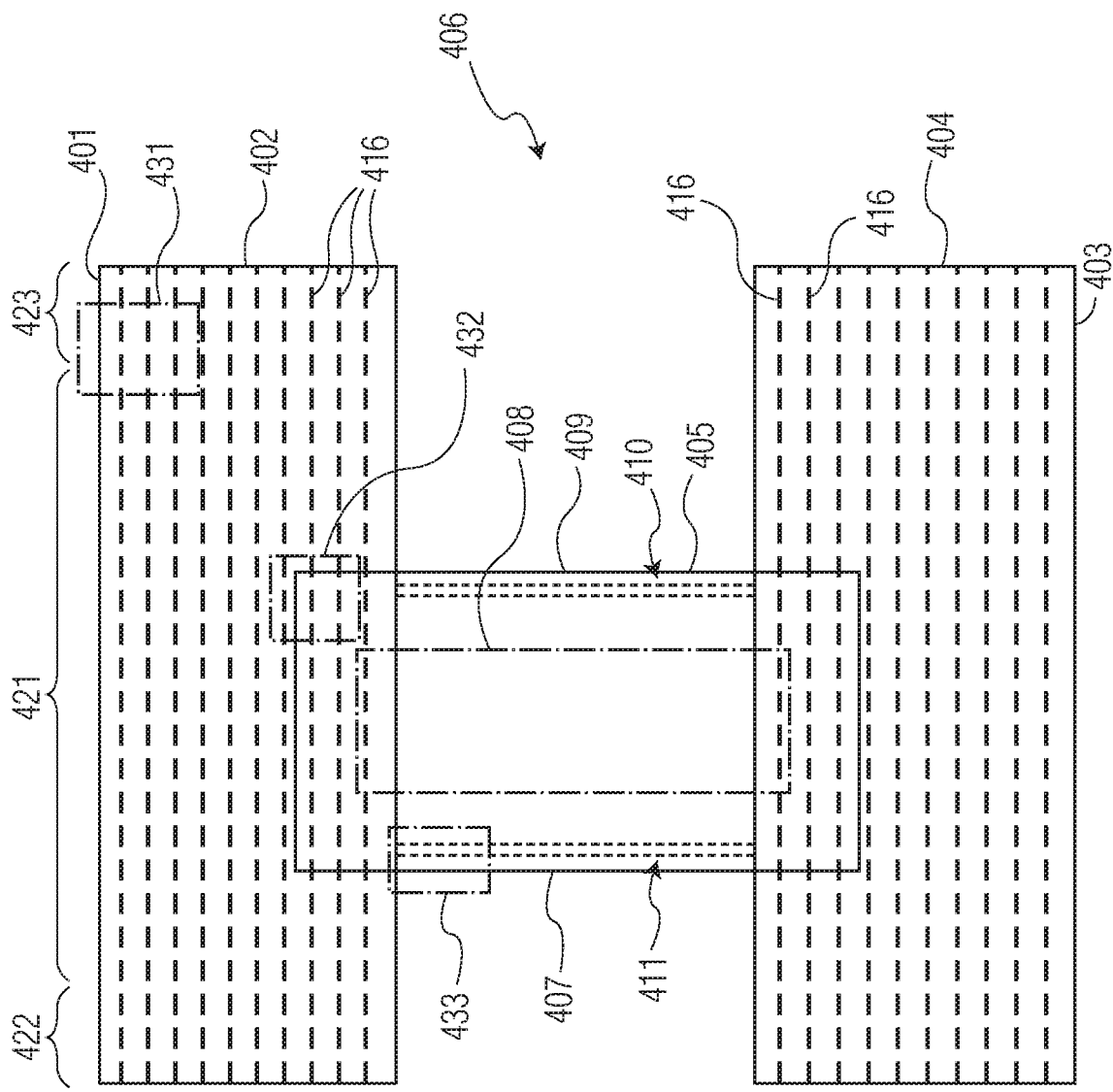
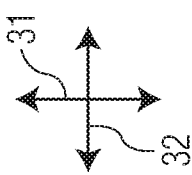
FIG. 7

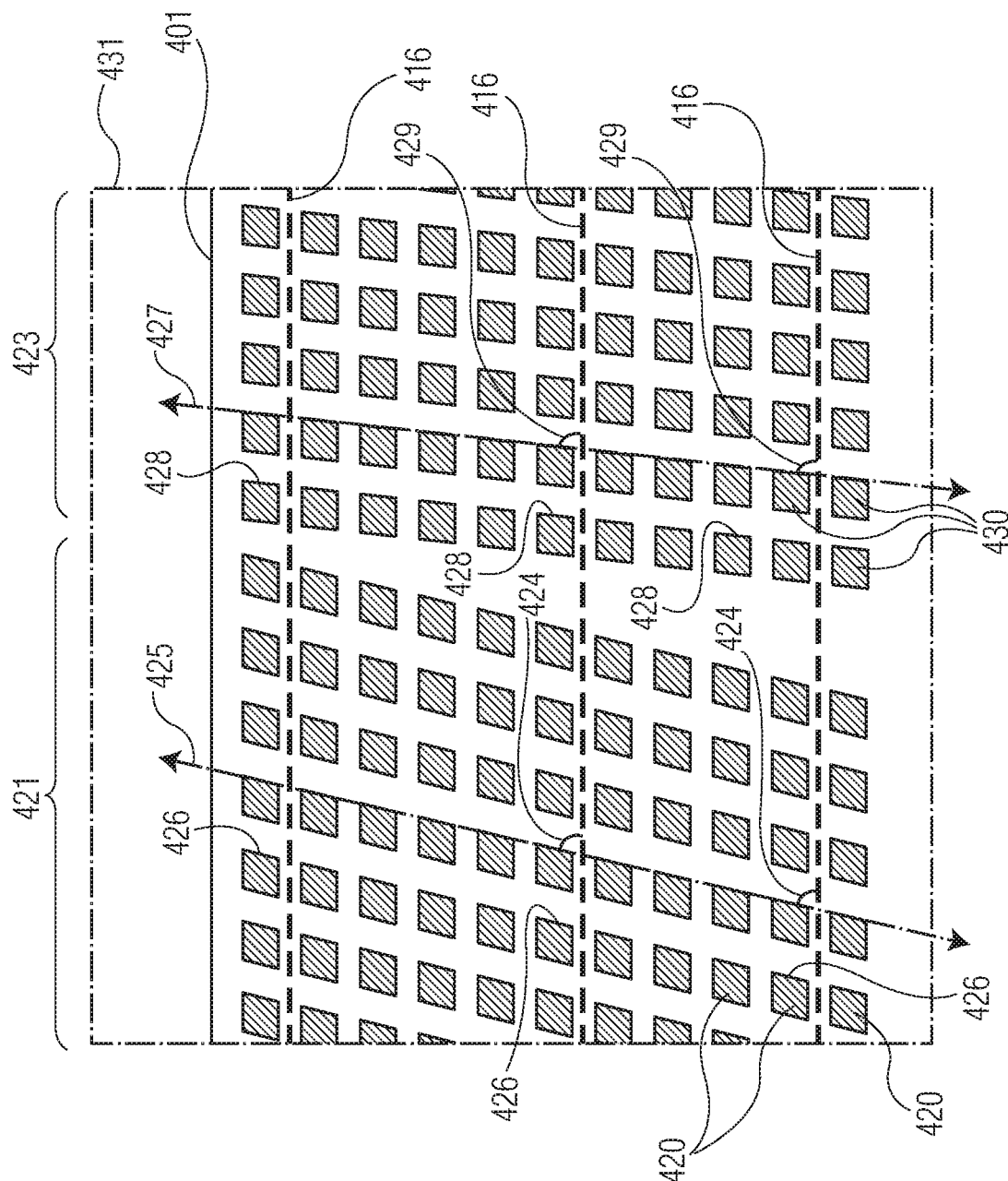
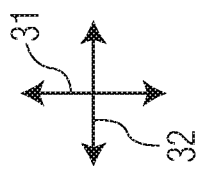
FIG. 8

ELASTICATED MATERIALS WITH DIRECTIONAL STRETCH PROPERTIES

CROSS-REFERENCE TO RELATED APPLICATION

This application claims the benefit of U.S. Provisional Application No. 62/464,640, filed Feb. 28, 2017.

TECHNICAL FIELD

The present disclosure relates to elasticated materials, and more specifically elasticated materials that have directional stretch properties.

BACKGROUND OF THE DISCLOSURE

Elasticated materials are used in many different applications, including within various clothing garments and absorbent articles. Such elasticated materials may be used as part of waistbands, leg cuffs, barrier cuffs, or in other components of clothing garments and absorbent articles to provide beneficial fit characteristics, help prevent leakage of bodily exudates, or impart other benefits.

Many present clothing garments and absorbent articles include elasticated materials which comprise elastic strands positioned between layers of material and affixed to the layers of material with adhesive. Some prior art elasticated materials have attempted to remove the adhesive in favor of affixing the elastic strands to the layers of material with the use of discrete individual bonds. These prior art materials position the bonds across the elastic strands a distance less than the un-tensioned diameter of the elastic strands. Some example prior art materials can be seen in U.S. Pat. No. 6,291,039 to Cera France Compagnie d'Equipment Robotique Appliquee, titled "Ruffling Slide and Method for Making Same". This particular structural configuration holds the elastic strands in place within the elasticated material between the bonds. These adhesive-less elasticated materials have a cost advantage as they do not require adhesive to affix the elastomeric strands within the elasticated material. Accordingly, additional elasticated materials which do not include adhesive may be desired to help reduce overall costs of absorbent articles, in addition to having functional benefits.

SUMMARY OF THE DISCLOSURE

The present disclosure relates to elasticated materials, and more specifically elasticated materials that have directional stretch properties. In general, the elasticated materials of the present disclosure are constructed so that they have particular sets of desired stretch properties. For instance, an elasticated material of the present disclosure may have a first set of stretch properties along a first length of the material and a second set of stretch properties along a second length. Other elasticated materials of the present disclosure may have symmetric stretch properties and/or a continuous stretch property such that the elasticated material stretches in all directions. These different stretch properties can be targeted within specific areas of an absorbent article or clothing garment, such as in a waistband or in the leg elastics, in order to enhance an overall fit and function of the absorbent article or garment In a first embodiment, an elasticated material may comprise a first layer of material, a second layer of material bonded to the first layer of material by a first pair of bonds comprising a first bond and a second bond and a second pair of bonds comprising a third bond and a fourth bond, and a plurality of elastomeric strands extending in a lateral direction and disposed between the first layer of material and the second layer of material and separated in a longitudinal direction. The first bond and the second bond may be disposed on opposite sides of a first strand of the plurality of elastomeric strands and may be separated by a longitudinal distance less than an un-tensioned diameter of the first strand. The third bond and the fourth bond may be disposed on opposite sides of a second strand of the plurality of elastomeric strands and may be separated by a longitudinal distance less than an un-tensioned diameter of the second strand. The first bond and the third bond may also be located on a first side of the first strand and the second strand, respectively, and the second bond and the fourth bond may be located on a second side of the first strand and the second strand, respectively. Additionally, the first bond and the third bond may comprise first side portions and second side portions, the first side portion of the first bond may form a first angle with respect to the first strand of the plurality of elastomeric strands, and the first side portion of the third bond may form a second angle with respect to the second strand of the plurality of elastomeric strands. In at least some embodiments, the first angle may be different than the second angle.

In a second embodiment, the elasticated material of the first embodiment may comprise a third pair of bonds comprising a fifth bond and a sixth bond, and the fifth bond and the sixth bond may be located on opposite sides of a third elastic strand of the plurality of elastic strands and be separated by a longitudinal distance less than an un-tensioned diameter of the third strand. The first bond, the third bond, and the fifth bond may all be located on the first side of the first strand, the second strand, and the third strand, respectively, and the second bond, the fourth bond, and the sixth bond may all be located on the second side of the first strand, the second strand, and the third strand, respectively. Additionally, the first bond, the third bond, and the fifth bond may comprise first side portions and second side portions, and the first side portion of the fifth bond may form a third angle with respect to the third strand of the plurality of elastomeric strands. Further, the first angle, the second angle, and the third angle may all be different.

In a third embodiment, the elasticated material of the first embodiment may further comprise a third pair of bonds comprising a fifth bond and a sixth bond, and the fifth bond and the sixth bond may be located on opposite sides of a third elastic strand of the plurality of elastic strands and be separated by a longitudinal distance less than an un-tensioned diameter of the third strand. The first bond, the third bond, and the fifth bond may also all be located on the first side of the first strand, the second strand, and the third strand, respectively, and the second bond, the fourth bond, and the sixth bond may all be located on the second side of the first strand, the second strand, and the third strand, respectively. The first bond, the third bond, and the fifth bond may comprise first side portions and second side portions, and the first side portion of the fifth bond may form a third angle with respect to the third strand of the plurality of elastomeric strands. Additionally, the first angle and the third angle may be the same while the second angle is different from the first angle and the third angle.

In a fourth embodiment, the second strand of the plurality of elastomeric strands of the third embodiment may be positioned longitudinally between the first strand of the plurality of elastomeric strands and the third strand of the plurality of elastomeric strands.

In a fifth embodiment, the first angle of any of the first through fourth embodiments may be less than 90 degrees, and the second angle may be greater than 90 degrees.

In a sixth embodiment, the second angle of the fifth embodiment may have a value in degrees that is 180 minus the value of the first angle.

In a seventh embodiment, the first angle of any of the first through sixth embodiments may be between about 30 degrees and about 89 degrees, and the second angle may be between about 95 degrees and about 145 degrees.

In an eighth embodiment, the first angle of any of the first through seventh embodiments may be between about 50 degrees and about 88 degrees, and the second angle may be between about 115 degrees and about 135 degrees.

In a ninth embodiment, the first layer of material and the second layer of material of any of the first through eighth embodiments may be comprised of separate webs of material.

In a tenth embodiment, the elasticated material of any of the first through ninth embodiments may further comprise a third pair of bonds comprising a fifth bond and a sixth bond disposed on opposite sides of the first strand of the plurality of elastomeric strands and separated by a longitudinal distance less than the un-tensioned diameter of the first strand. The first pair of bonds and the third pair of bonds may be spaced apart along the first strand of the plurality of elastomeric strands. The first bond and the fifth bond may be located on the first side of the first strand of the plurality of elastomeric strands and the second bond and the sixth bond may be located on the second side of the first strand of the plurality of elastomeric strands. Additionally, the first bond and the fifth bond may comprise first side portions and second side portions with the first side portion of the fifth bond forming a third angle with respect to the first strand of the plurality of elastomeric strands, and the first angle may be different than the third angle.

In an eleventh embodiment, the elasticated material of the tenth embodiment may further comprise a fourth pair of bonds comprising a seventh bond and an eighth bond disposed on opposite sides of the second strand of the plurality of elastomeric strands and separated by a longitudinal distance less than the un-tensioned diameter of the second strand. The second pair of bonds and the fourth pair of bonds may be spaced apart along the second strand of the plurality of elastomeric strands, while the third bond and the seventh bond may be located on the first side of the second strand of the plurality of elastomeric strands and the fourth bond and the eighth bond may located on the second side of the second strand of the plurality of elastomeric strands. The third bond and the seventh bond may comprise first side portions and second side portions, and the first side portion of the seventh bond may form a fourth angle with respect to the second strand of the plurality of elastomeric strands. Additionally, the second angle may different than the fourth angle, and the third angle may be different than the fourth angle.

In a twelfth embodiment, the third angle of the eleventh embodiment may be less than 90 degrees, and the fourth angle may be greater than 90 degrees.

In a thirteenth embodiment, an absorbent article may include a front waist region having a front waist edge, a rear waist region having a rear waist edge, a crotch region, a longitudinal axis and a lateral axis. The absorbent article may further comprise a chassis including an absorbent body, the chassis including a body facing surface and a garment facing surface, a topsheet; and a rear waistband. The rear waistband may comprise a first plurality of elastomeric strands extending in a lateral direction and disposed between a first layer of material and a second layer of material and separated in a longitudinal direction, a first bond and a second bond disposed on opposite sides of a first strand of the first plurality of elastomeric strands and separated by a longitudinal distance less than an un-tensioned diameter of the first strand, and a third bond and a fourth bond disposed on opposite sides of a second strand of the first plurality of elastomeric strands and separated by a longitudinal distance less than an un-tensioned diameter of the second strand. The first bond and the third bond may be located on a first side of the first strand of the first plurality of elastomeric strands and the second strand of the first plurality of elastomeric strands, respectively, and the second bond and the fourth bond may be located on a second side of the first strand of the first plurality of elastomeric strands and the second strand of the first plurality of elastomeric strands, respectively. Additionally, the first bond and the third bond may comprise first side portions and second side portions with the first side portion of the first bond forming a first angle with respect to the first strand of the first plurality of elastomeric strands and the first side portion of the third bond forming a second angle with respect to the second strand of the first plurality of elastomeric strands. Further, the first angle may be different than the second angle.

In a fourteenth embodiment, the first layer of material and the second layer of material of the thirteenth embodiment may comprise a first layer of the chassis and a second layer of the chassis, and the first plurality of elastomeric strands may be disposed between the first layer of the chassis and a second layer of the chassis within the rear waist region of the absorbent article to form the rear waistband.

In a fifteenth embodiment, the absorbent article of the thirteenth or fourteenth embodiments may further comprise a front waistband comprising a second plurality of elastomeric strands extending in the lateral direction and disposed between a third layer of material and a fourth layer of material and separated in the longitudinal direction, a fifth bond and a sixth bond disposed on opposite sides of a first strand of the second plurality of elastomeric strands and separated by a longitudinal distance less than an un-tensioned diameter of the first strand, and a seventh bond and an eighth bond disposed on opposite sides of a second strand of the second plurality of elastomeric strands and separated by a longitudinal distance less than an un-tensioned diameter of the second strand. The fifth bond and the seventh bond may be located on a first side of the first strand of the second plurality of elastomeric strands and the second strand of the second plurality of elastomeric strands, respectively, and the sixth bond and the eighth bond may be located on a second side of the first strand of the second plurality of elastomeric strands and the second strand of the second plurality of elastomeric strands, respectively. Additionally, the first bond and the third bond may comprise first side portions and second side portions with the first side portion of the first bond forming a first angle with respect to the first strand of the second plurality of elastomeric strands and the first side portion of the third bond forming a second angle with respect to the second strand of the second plurality of elastomeric strand. Further, the first angle is different than the second angle.

In a sixteenth embodiment, the third layer of material and the fourth layer of material of the fifteenth embodiment may comprise a first layer of the chassis and a second layer of the chassis, and the second plurality of elastomeric strands may be disposed between the first layer of the chassis and a second layer of the chassis within the front waist region of the absorbent article to form the front waistband.

In a seventeenth embodiment, the first angle of any of the thirteenth through sixteenth embodiments may be less than 90 degrees, and the second angle may be greater than 90 degrees.

In an eighteenth embodiment, the second angle may have a value in degrees that is 180 minus the value of the first angle.

In a nineteenth embodiment, a portion of the chassis in the front waist region and a portion of the chassis in the rear waist region of any of the thirteenth through eighteenth embodiments may be bonded together.

In a twentieth embodiment, an elasticated material may comprise a first web material, a second web material bonded to the first web material by a plurality of bonds, and a plurality of elastomeric strands extending in a lateral direction perpendicular to a longitudinal direction and disposed between the first web material and the second web material. The plurality of bonds may comprise a first pair of bonds comprising a first bond and a second bond and a second pair of bonds comprising a third bond and a fourth bond. The first bond and the second bond may be disposed on opposite sides of a first elastomeric strand of the plurality of elastomeric strands with the first bond and the second bond being separated by a longitudinal distance less than an un-tensioned diameter of the first elastomeric strand of the plurality of elastomeric strands, and the third bond and the fourth bond may be disposed on opposite sides of a second elastomeric strand of the plurality of elastomeric strands with the third bond and the fourth bond being separated by a longitudinal distance less than an un-tensioned diameter of the second elastomeric strand of the plurality of elastomeric strands. Additionally, the elasticated material may exhibit greater than 1% elongation in the longitudinal direction under an applied force in the longitudinal direction at every angle of rotation of the elasticated material with respect to the longitudinal direction.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which:

FIG. 7 is a plan view of an exemplary absorbent article including elasticated materials according to aspects of the present disclosure;

FIG. 8 is a plan view of an exemplary elasticated material that may comprise a portion of a waistband of the absorbent article of FIG. 7;

Figure 1:
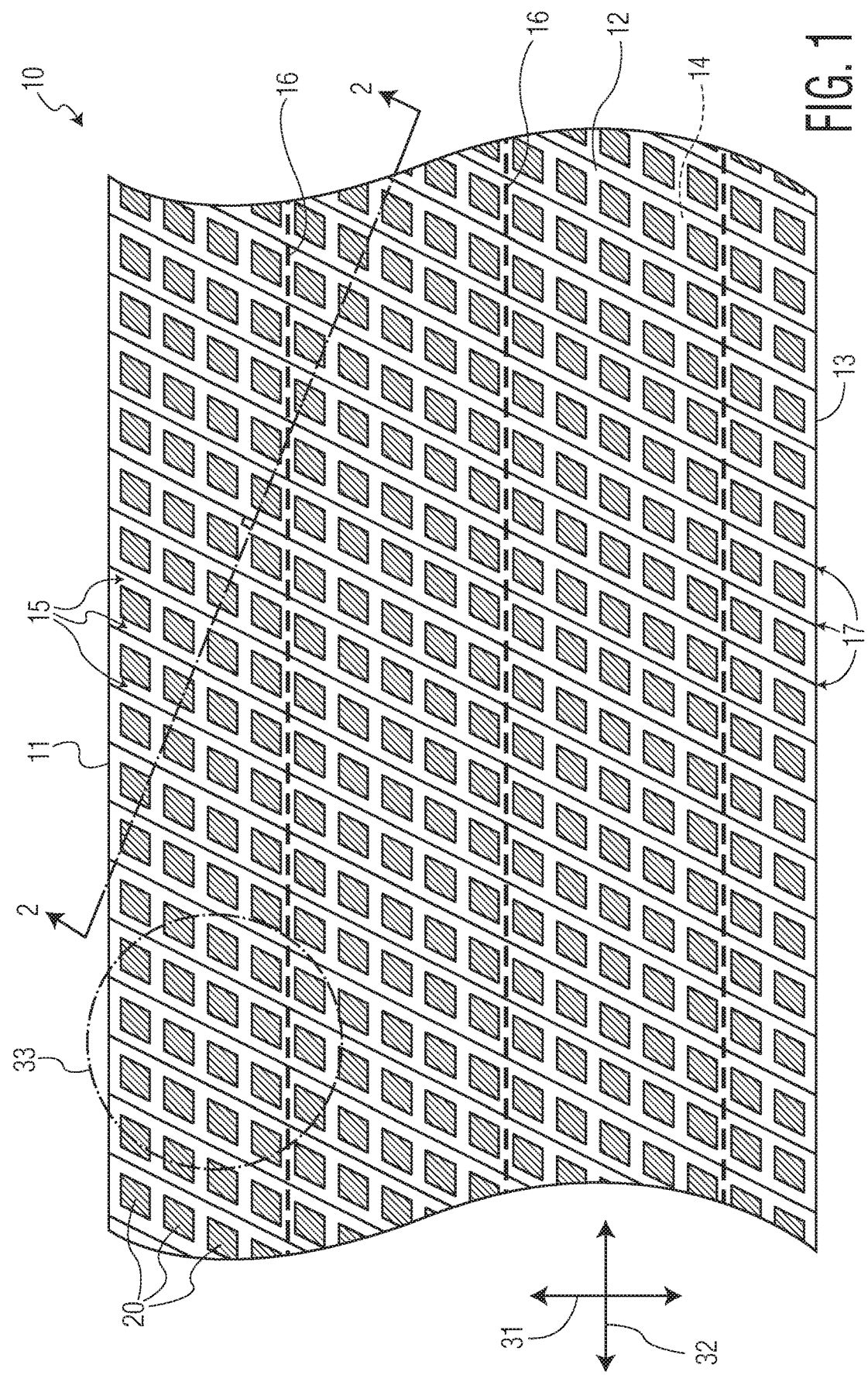
FIG. 1 is a plan view of an elasticated material according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed toward elasticated materials that have directional stretch properties. The elasticated materials may not require adhesive to affix the elastomeric strands of the material within the material. Although, it should be understood that in some embodiments, the elasticated materials disclosed herein may benefit from applications of adhesive as well. Additionally, the particular shape and/or location of the bonds can be used to impart different stretch properties along different portions of the elasticated material, or to impart a symmetric and/or a continuous stretch property to the material. The present disclosure details a number of different materials that can be formed by employing differently shaped bonds along different portions of a material, and how the elasticated materials can be used in clothing garments and in absorbent articles to enhance fit and/or function of the article.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

DEFINITIONS

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40.

Spunbond fibers are generally not tacky when they are deposited on a collecting surface.

The term "elasticated" when used herein to describe a material or a portion of an article means that the material or article it is made of an inelastic sheet material coupled to elastomeric material, e.g. one or more elastomeric bands or strands, such that the material or article exhibits elastic properties.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Elasticated Material:

FIG. 1 is a top plan view depicting a portion of exemplary elasticated material 10. The elasticated material 10 generally extends in both the longitudinal direction 31, between a top sheet edge 11 and a bottom sheet edge 13, and the lateral direction 32. The elasticated material 10 may generally comprise a first layer of material 12, a second layer of material 14, elastomeric strands 16, and bonds 20. As will be described in more detail below, at least some of the bonds 20 may be positioned on opposite sides of the elastomeric strands 16 in such a manner that the bonds 20 affix, or "entrap", portions of the elastomeric strands 16 in place within the elasticated material 10.

Figure 2:
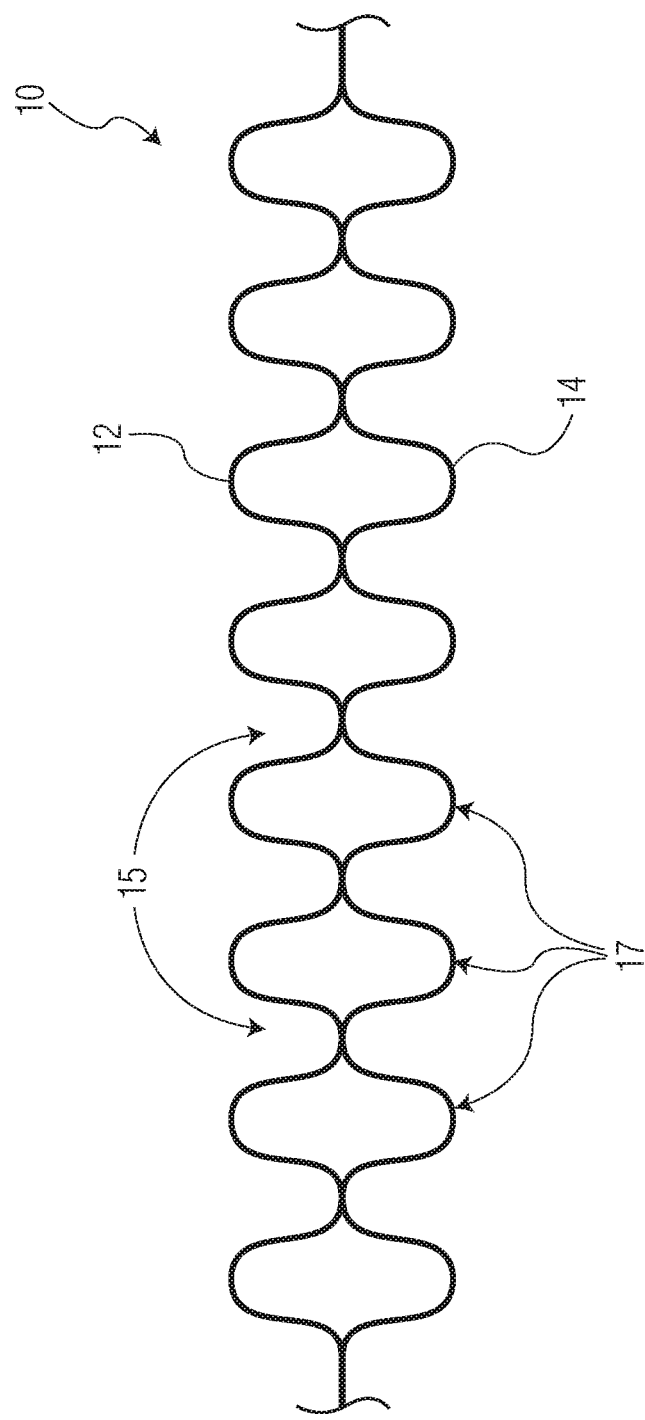
FIG. 2 is a cross-section of the elasticated material of FIG. 1 as viewed along line 2-2 v.

In at least some embodiments, the elasticated material 10 may be formed with the elastomeric strands 16 in a stretched state. When the elasticated material 10 is allowed to relax, the elastomeric strands 16 contract between the entrapped portions causing valleys 15 and ridges 17 to form within the elasticated material 10. The structure of the elasticated material 10, including the valleys 15 and the ridges 17, may be seen more clearly in FIG. 2, which is a cross-section of the elasticated material 10 of FIG. 1, as viewed along line 2-2, which is drawn perpendicular to the ridges 15 and valleys 17 of the elasticated material 10.

Figure 3A:
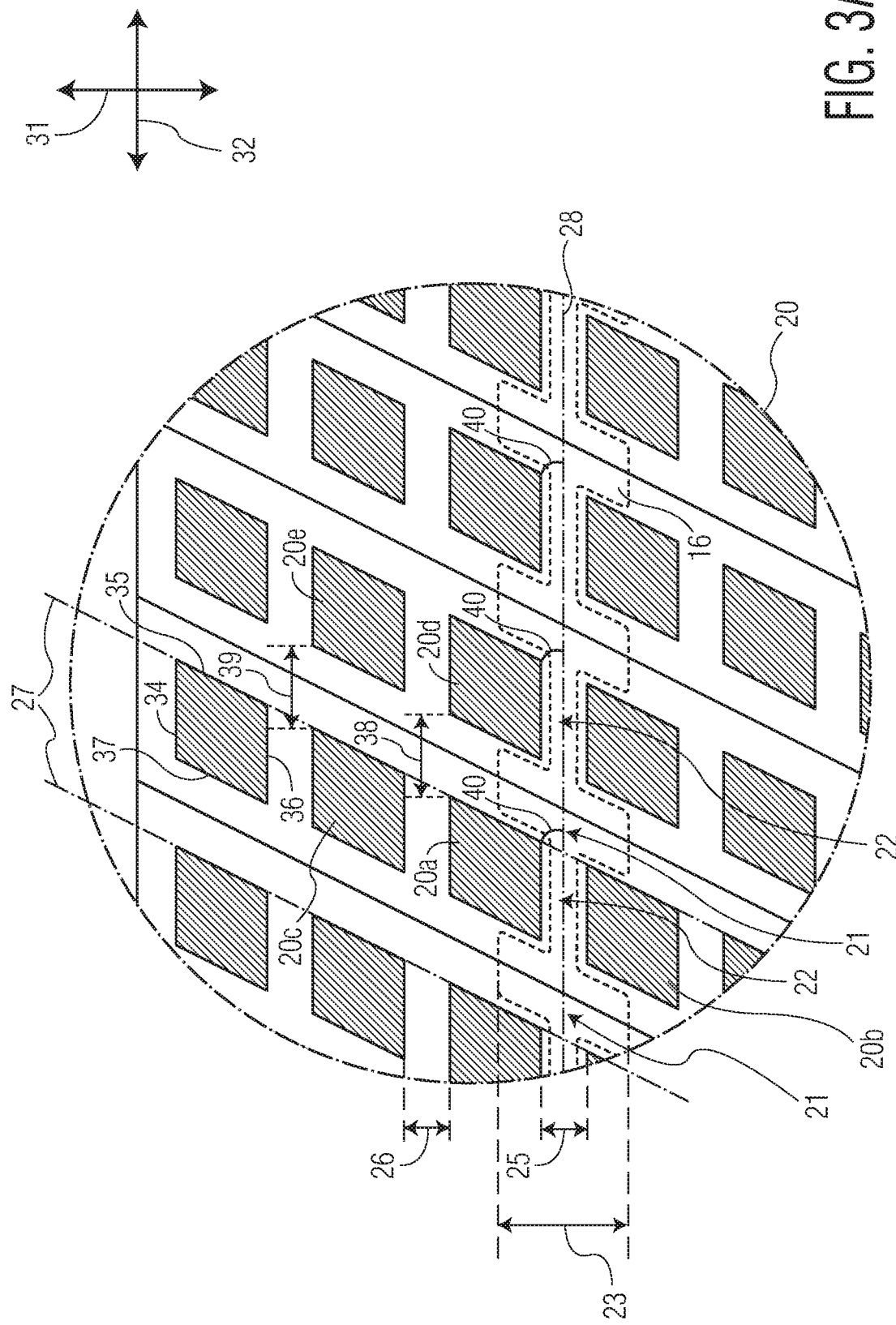
FIG. 3 is a plan view of a close-up of a portion of the elasticated material of FIG. 1.

FIG. 3A depicts a close-up view of circle 33 of FIG. 1, detailing the bonds 20 and one of the elastomeric strands 16 of the elasticated material 10 in more detail. Specifically, FIG. 3A depicts with dashed lines the outer edges of the elastomeric strand 16 as it passes between the bonds 20, including bonds 20a and 20b which entrap the strand 16. As can be seen, the elastomeric strand 16 in FIG. 3A may have non-entrapped portions 21 and entrapped portions 22, which alternate along the lateral length of the elastomeric strand 16.

In order to form a material such as the elasticated material 10, with elastomeric strands 16 comprising non-entrapped portions 21 and entrapped portions 22, the elastics strands 16 may be stretched before or as the elastomeric strands 16 are positioned between the first layer of material 12 and the second layer of material 14. The elastomeric strands 16 may have an un-tensioned outer diameter, and the outer diameter of the elastomeric strands 16 may decrease as the strands 16 are stretched. Accordingly, before or at the time the strands 16 are placed between the first layer of material 12 and the second layer of material 14, the elastomeric strands 16 may have an outer diameter that is less than the un-tensioned outer diameter of the elastomeric strands 16. Then, at least some of the bonds 20 of the material 10, for example bonds 20a, 20b in FIG. 3A, may be placed on opposite sides of the stretched elastomeric strands 16 and spaced apart longitudinally across the elastomeric strands 16 a longitudinal distance 25. In some embodiments, the longitudinal distance 25 may be approximately equal to the outer diameter of the strands 16 at the time the bonds 20a, 20b are formed. In other embodiments, the longitudinal distance 25 may be greater than the outer diameter of the strands 16 at the time the bonds 20a, 20b are formed, but less than the outer diameter of the un-tensioned diameter of the strands 16.

As the elastomeric strands 16 are allowed to relax, the outer diameter of the elastomeric strands 16 generally increases back toward the un-tensioned outer diameter of the elastomeric strands 16. However, as can be seen in FIG. 3A, this expansion is inhibited in the entrapped portions 22 of the elastomeric strands 16 by the bonds 20 which are positioned across the strands 16 a longitudinal distance less than the un-tensioned diameter of the strands 16, such as bonds 20a, 20b. As the elastic strand 16 of FIG. 3A relaxes and contracts from a stretched state, the non-entrapped portions 21 of the elastomeric strands 16 expand in the longitudinal direction (e.g. the outer diameter of the elastomeric strand 16 increases), resulting in the structure as seen in FIG. 3A with the elastic strand 16 shown having expanded outer diameter 23 in the non-entrapped portions 21.

In some embodiments, the expanded diameter 23 may be the same as the un-tensioned diameter of the elastic strand 16, but in other embodiments this may not be the case. For example, the specific configuration of the type of elastic strand 16, the amount of elongation of the elastic strand 16 in the forming process, and the location of the bonds 20 in relation to the elongated elastic strand 16, both in the longitudinal distance 25 between bonds 20 that span the elastomeric strand 16 and in the lateral distance between bonds 20, may prevent the diameter of the elastic strand 16 from expanding in the non-entrapped portions 21 all the way back to the un-tensioned diameter of the strand 16. Accordingly, in some embodiments the expanded diameter 23 in the non-entrapped portions 21 of at least some of the elastic strands 16 of the material 10 may still be less than the un-tensioned diameter of the elastic strands 16.

Web Materials:

In general, the first layer of material 12 and the outer layer of material 14 may be constructed of any materials suitable for use in waistbands, leg cuffs, or any other body-contacting portions, or non-body-contacting portions, of clothing garments and absorbent articles. The layers 12, 14 may be constructed of the same material or different materials. Each of the layers 12, 14 may comprise a single layer, multiple layers, laminates, or the like in different contemplated embodiments. Additionally, the layers 12, 14 may comprise two separate webs of material positioned on opposite sides of the elastomeric strands 16 to form the elasticated material 10, or the layers 12, 14 may comprise a single web of material that is folded over such that a first portion of the web of material is positioned on a first side of the elastomeric strands 16 and a second portion of the web of material is positioned on a second side of the elastomeric strands 16 to form the elasticated material 10.

Exemplary suitable classes of materials for the layers 12, 14, include synthetic fibers (for example, polyethylene or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Additionally, various woven and non-woven fabrics can be used for the layers 12, 14. The layers 12, 14 can comprise woven fabrics, nonwoven fabrics, polymer films, film-fabric laminates or the like, as well as combinations thereof. Examples of nonwoven fabrics can include spunbond fabrics, meltblown fabrics, coform fabrics, carded webs, bonded-carded webs, bicomponent spunbond fabrics, spunlaces, or the like, as well as combinations thereof.

For example, the layers 12, 14 can be composed of a meltblown or spunbond webs of polyolefin fibers. Alternatively, the layers 12, 14 can be bonded-carded webs composed of natural and/or synthetic fibers. The layers 12, 14 can be composed of a substantially hydrophobic materials, and the hydrophobic materials can, optionally, be treated with a surfactant or otherwise processed to impart a desired level of wettability and hydrophilicity. The surfactant can be applied by any conventional means, such as spraying, printing, brush coating or the like. The surfactant can be applied to the entirety of the layers 12, 14 or it can be selectively applied to particular sections of the layers 12, 14. Some specific exemplary materials suitable for the layers 12, 14 include 100% polypropylene bonded-carded webs in the 5-150 gsm range. Other exemplary suitable materials include spunbond polypropylene non-woven webs in the 5-150 gsm range. Still other exemplary materials may have basis weights above 150 gsm.

In an embodiment, the layers 12, 14 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, the layers 12, 14 can be spunbond substrates with a basis weight from about 8 to about 50 gsm. In an embodiment, the layers 12, 14 can be a 12 gsm spunbond-meltblown-spunbond substrate. In another embodiment, the layers 12, 14 can be an 8 gsm spunbond-meltblown-spunbond substrate.

Elastomeric Strands:

Suitable elastomeric materials for the elastomeric strands 16 can include, but are not limited to, spandex elastomeric strands, strands of natural or synthetic rubber, thermoplastic elastomeric materials, or heat activated elastomeric materials. The elastomeric strands 16 can be any elastomeric material capable of being elongated at least about 50 percent, desirably about 350 percent, and capable of recovering to within at least about 250 percent, and desirably about 150 percent of its original length after being elongated about 300 percent. The elastomeric strands 16 can be a spandex elastomeric strand(s) such as, for example, a LYCRA thread commercially available from E. I. DuPont de Nemours and Co. Alternatively, the elastomeric strands 16 can be composed of a thermoplastic elastomer or a natural or a synthetic rubber commercially available from J.P.S. Elastomerics Corp. Alternatively, the elastomeric strands 16 can also be composed of a heat activated elastic material such as PEBAX, commercially available from Atochem, Inc., which can be activated with heat treatment after the elastomeric strands 16 have been disposed within the elasticated material 10 and the bonds 20 have been formed. In at least some embodiments, the elastomeric strands may have diameters that range between about 10 denier to about 1500 denier.

Bonds:

The bonds 20 can be formed through any suitable bonding technique, such as thermal/heat bonding, ultrasonic bonding, pressure bonding, or other known bonding techniques. In general, as will be described in more detail below, the bonds 20 can be formed by use of a pattern component and a smooth component. To form the bonds 20, the layers 12, 14, with the elastomeric strands 16 disposed therebetween, are positioned between the pattern component and the smooth component with appropriate alignment between any features of the pattern component and the elastomeric strands 16. For instance, the elastomeric strands 16 may be positioned between raised protrusions of the pattern component.

For instance, where thermal bonding, pressure bonding, or rotary ultrasonic bonding techniques are used to form the bonds 20, the pattern component and the smooth component may be pattern rolls and smooth rolls, respectively. In such embodiments, the pattern rolls may contain a number of raised portions that protrude from the surface of the pattern rolls. The raised portions may correspond approximately with the shape of the bonds 20 and aligned on the surface of the pattern rolls to produce the longitudinal and latitudinal alignment of the bonds 20 as depicted in the different embodiments of the elasticated materials of the present disclosure. The smooth rolls may generally be solid rolls with smooth outer surfaces.

The heat bonding techniques which may be used to form the bonds 20 may include heating the raised portions of the pattern rolls to between about 70 degrees C. and about 340 degrees C. In general, the level of heating should be less than that which results in melting of the elastic strands 16 when the bonds are being formed. While the raised portions are at the appropriate temperature, the pattern roll may be pressed onto the smooth roll, with the layers 12, 14 and the elastomeric strands 16 positioned between the rolls. As some examples, the compressive force used to form the bonds 20 may be between about 500 KPa and about 2,750 KPa, and the layers 12, 14 and the elastomeric strands 16 may pass between the pattern and anvil rolls between about 100 linear meters per minute (mpm) and about 350 (mpm).

The rotary ultrasonic bonding techniques that may be used to form the bonds 20 may use ultrasonic energy in order to form the bonds 20. For instance, as the layers 12, 14 and the elastomeric strands 16 pass between the pattern roll and smooth roll of a rotary ultrasonic bonder, the smooth roll may be vibrated at a frequency of between about 20,000 Hz and about 50,000 Hz, causing internal heating of the layers 12, 14 to such an extent that the layers 12, 14 melt together forming the bonds 20.

The pressure bonding techniques which may be used to form the bonds 20 may be similar to the heat bonding techniques described above, except that no external heat may need to be applied to the raised portions of the pattern roll. However, in order to compensate for the raised portions only being at an ambient temperature, the compressive force applied to the pattern roll and the smooth roll to form the bonds 20 must be greatly increased. In some examples, the compressive force is applied to produce a nip force between about 0.1 KN and about 5 KN, while the layers 12, 14 and the elastomeric strands 16 pass between the pattern roll and the anvil roll at about 15 mpm and 450 mpm.

In non-rotary ultrasonic bonding techniques that may be used to form the bonds 20, the pattern element and the anvil element may be a smooth ultrasonic horn and a patterned anvil. In such embodiments, the anvil component may have the raised portions, while the ultrasonic horn has a generally smooth surface. Like with the rotary ultrasonic techniques, the ultrasonic horn may be vibrated at a frequency of between about 20,000 Hz and about 50,000 Hz, as the layers 12, 14 and the elastomeric strands 16 pass between the ultrasonic horn and the patterned anvil. This ultrasonic energy application causes internal heating of the layers 12, 14 to such an extent that the layers 12, 14 melt together forming the bonds 20.

In general, such heat bonding techniques, ultrasonic bonding techniques, and pressure bonding techniques known in the art. It should be understood that the parameters described for the different techniques are only exemplary suitable parameters. The described techniques may be used to form the bonds 20 using such techniques operating with other suitable parameters, as is known in the art. For instance, PCT Patent Application WO 2010/068150, titled "METHOD AND APPARATUS FOR BONDING", which is incorporated herein by reference in its entirety, details methods and apparatus for performing pressure bonding which could be used to form the bonds 20 of the bond patterns described in the present disclosure using many different suitable parameters. It should additionally be understood that the different ways in which the bonds 20 are formed do not appreciably affect the resulting structure of the elasticated material, aside from possibly resulting in different strengths of bonds. However, all of such known techniques are capable of producing bonds which are strong enough to resist the expansion of the elastomeric strands positioned between the bonds without breaking. Accordingly, the bonds 20 may be formed according to any known bonding technique without departing from the scope of the present disclosure.

In general, the bonds 20 of the elasticated materials of the present disclosure may have any suitable size or shape. However, in at least some embodiments, the bonds may range between about 50 square micrometers to about 20 square millimeters, or between about 70 square micrometers to about 10 square millimeters, or between about 250 square micrometers and about 5 square millimeters. Additionally, in some embodiments, the dimension of the bonds 20 in a direction generally parallel to the elastomeric strands 16 may be between about two times to about six times greater than the dimension of the bonds 20 that is generally perpendicular to the elastomeric strands 16. For instance, in the embodiment of FIG. 3A, a lateral dimension of the bonds 20 may be between about two times and about six times greater than a longitudinal dimension 31 of the bonds 20.

Additionally, it should also be understood that the bonds may generally have any longitudinal and/or lateral spacing. For instance, the longitudinal spacing of longitudinally adjacent bonds of the bonds 20, such as 20a and 20b or 20a and 20c of FIG. 3A, may vary depending on whether an elastomeric strand 16 is disposed between the longitudinally adjacent bonds. In some embodiments, the longitudinal spacing between longitudinally adjacent bonds 20a and 20b, as represented by longitudinal distance 25, may be less than the longitudinal spacing between longitudinally adjacent bonds 20b and 20c, represented by longitudinal distance 26, where no elastomeric strand 16 is disposed between bonds 20a, 20c. As an example, the longitudinal spacing between longitudinally adjacent bonds 20a, 20b may be less than the un-tensioned diameter of the elastomeric strand 16, while the longitudinal spacing between longitudinally adjacent bonds 20a, 20c may have any suitable longitudinal spacing including a spacing that is greater than the un-tensioned diameter of any elastomeric strands 16 of the material 10. As some illustrative examples, the longitudinal spacing of longitudinally adjacent bonds where no elastomeric strand 16 is disposed between the longitudinally adjacent bonds (such as bonds 20a, 20c) may vary between about 1 mm and about 500 mm.

The lateral spacing between laterally adjacent bonds of the bonds 20 may be the same throughout the material 10, or may be varied. For instance, in some embodiments the lateral spacing between laterally adjacent bonds which are located adjacent an elastomeric strand 16 (e.g. bonds 20a, 20d), as represented by lateral distance 38, may be less than the lateral spacing between laterally adjacent bonds which are not located adjacent an elastomeric strand 16 (e.g. bonds 20c, 20e), as represented by lateral distance 39. Additionally, in some embodiments, the lateral spacing between laterally adjacent bonds may vary even between pairs of laterally adjacent bonds which are not adjacent an elastomeric strand 16. For instance, when used in a garment or absorbent article, the lateral spacing of bonds 20 may be varied throughout different regions of the garment or article to impart a desired pattern or softness to the material. As some non-limiting examples, the lateral spacing between laterally adjacent bonds of the bonds 20 may vary between about 1 mm and about 500 mm.

FIG. 3A details additional features of bonds 20. For instance, bonds 20 may each include a top portion 34, a bottom portion 36 opposite the top portion 34, a first side portion 35, and a second side portion 37 opposite the first side portion 35. As can be seen, in at least some embodiments, the first side portions 35 of the bonds 20 are angled with respect to the elastomeric strands 16. For instance, the first side portion 35 of bond 20a can be seen forming angle 40 with respect to a lateral axis 28 of the elastomeric strand 16. The angling of the first side portions 35 of the bonds 20 may provide the material 10 with desirable stretch properties, as will be explained in more detail herein. Additionally as can be seen, in at least some embodiments, the top portions 34 and the bottoms portions 36 of laterally adjacent bonds of the bonds 20 may generally align. However, in other embodiments, the top portions 34 and bottom portions 36 of laterally adjacent bonds may not generally align, and instead may be staggered.

Although shown as generally rectangular, and more specifically as parallelograms, the bonds 20 may be any suitable shape. For instance, the bonds 20 may be circular, semicircular, oval shaped, half-oval shaped, triangular, square, rectangular, trapezoidal, rhombus-shaped, or the like. In some embodiments, the bonds 20 can have three sides, four sides, five sides, six sides, or any other suitable number of sides.

In at least some embodiments, the bonds 20 may form generally longitudinally extending lines, as can be seen in FIG. 1. For instance, the first side portions 35 of longitudinally adjacent bonds of the bonds 20 may align to form bond lines 27 which coincide with the first side portion 35 of each longitudinally adjacent bond along a single bond line 27, as shown in FIG. 3A. The embodiment of FIG. 3A depicts bonds 20 as having first side portions 35 which form an angle 40 with respect to the lateral axis 28 of the elastomeric strand 16 and where the first side portions 35 of the bonds 20 are aligned along bond lines 27.

In the embodiments of FIG. 1 and FIG. 3A, the first side portions 35 of the bonds 20 comprise an entire side edge of the bonds 20. In other embodiments, the first side portions 35 of the bonds 20 may comprise vertices, for instance where the bonds 20 are rectangular and are oriented perpendicularly (see FIG. 3C) with respect to the elastomeric strands 16, or points on curved sides where the bonds 20 are circular or oval-shaped (see FIG. 3B). Accordingly, in general, the bonds 20 may be aligned, regardless of shape, such that a lateral-most point of the bonds 20, which form the first side portions 35, are aligned to form bond lines 27. For conciseness, the bonds of the elasticated materials of the present disclosure will be described as having side first side portions which form angles with respect to the elastic strands, but it should be understood that this is not intended to limit the scope of the present disclosure.

Figure 3B:
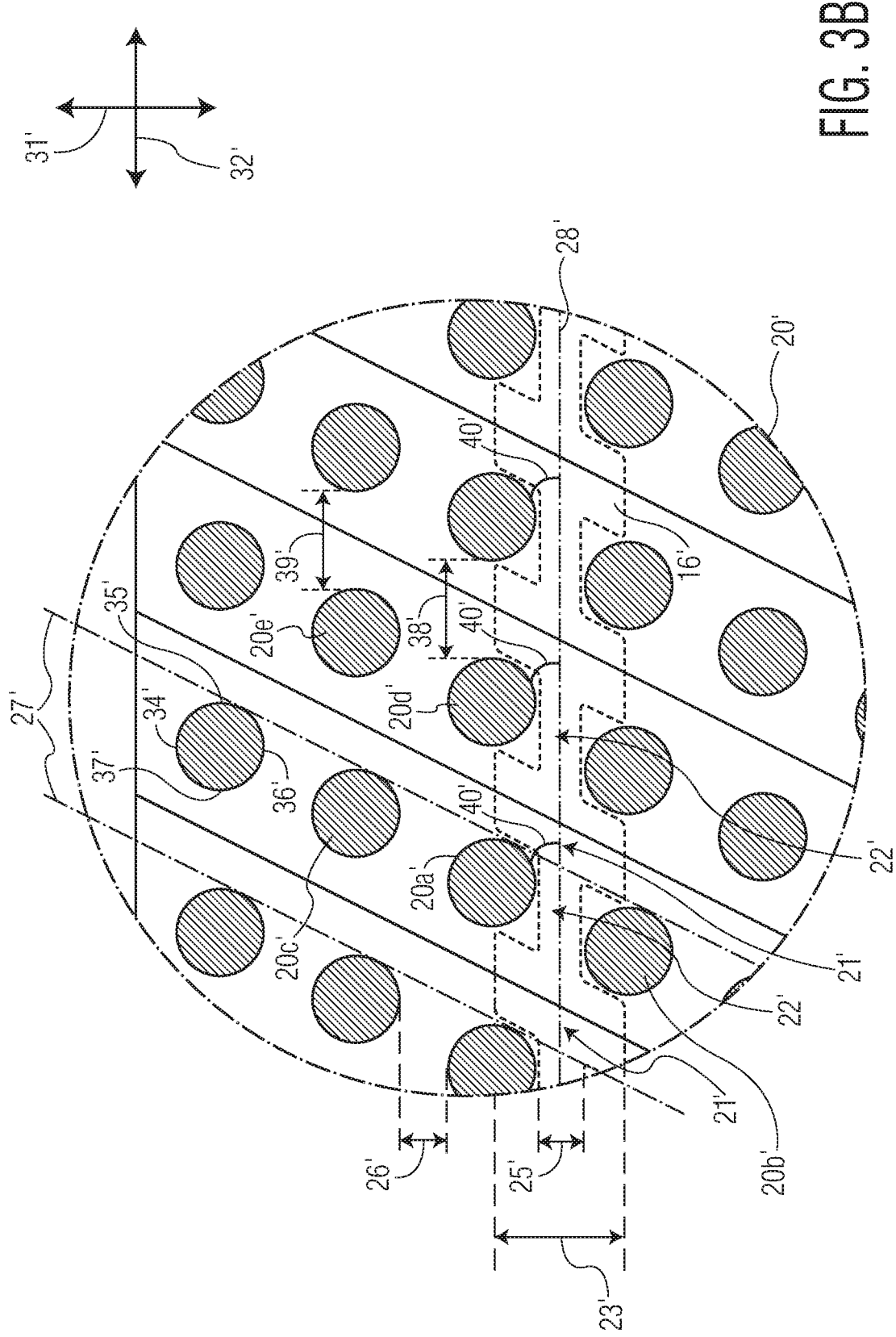
Figure 3C:
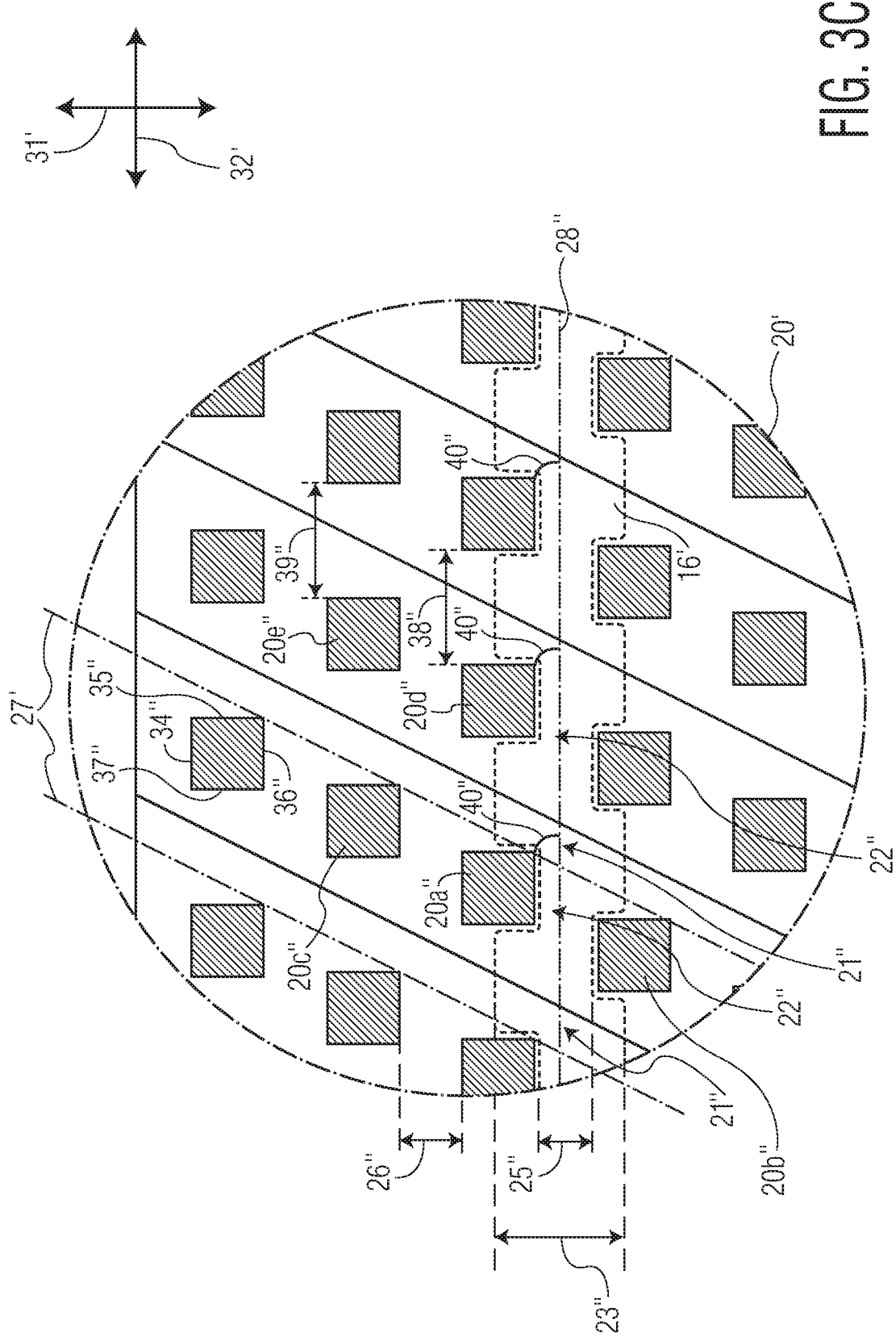

Accordingly, in embodiments such as the embodiments of FIGS. 3B and 3C, the first side portions 35', 35" of the bonds 20', 20" may not form an appreciable angle 40', 40" with respect to the lateral axis 28', 28" of the elastomeric strands 16'. In such embodiments, however, the bonds 20', 20" may be aligned along bond lines 27', and the bond lines 27' themselves may form an angle with respect to the lateral axis 28', 28" of the elastomeric strand 16'. The angles formed by the bond lines 27' with respect to the lateral axis 28', 28" of the elastomeric strand 16' may have values substantially similar to the values described herein with respect to angle 40. In these embodiments where the first side portions 35', 35" do not form an appreciable angle 40', 40" with respect to the lateral axis 28', 28" of the elastomeric strands 16' but the bond lines 27' do, the material 10 may still exhibit the beneficial stretch properties described herein. FIGS. 3B and 3C depict similar features of the material 10 with respect to FIG. 3A except the FIGS. 3B, 3C depict material 10 with the different bond shapes, as shown by bonds 20', 20". Accordingly, the features of the bonds 20', 20" and the material 10 depicted in FIGS. 3B, 3C are similar to those of FIG. 3A shown with similar reference numbers. For instance, FIG. 3A shows features noted by reference numbers 16, 20, 20a, 20b, 20c, 20d, 21, 22, 23, 25, 26, 27, 28, 34, 35, 36, 37, 38, 39, and 40, while the FIGS. 3B, 3C show the same features noted by reference numbers 16', 20', 20a', 20a", 20b', 20b", 20c', 20c", 20d', 20d", 21', 21", 22', 22", 23', 23", 25', 25", 26', 26", 27', 28', 28", 34', 34", 35', 35", 36', 36", 37', 37", 38', 38", 39', 39", and 40', 40", all respectively where there is a number with a prime and a number with a double prime.

It should be additionally understood that not every single bond 20 within a series of longitudinally adjacent bonds need to fully align into a bond line 27 in order for the material 10 to have the beneficial stretch properties described herein. For instance, in some embodiments the bonds 20 may be aligned generally along bond lines 27 where the first side portions 35 of at least some of the bonds 20 do not fall exactly on the bond lines 27. In some of these examples, the first side portions 35 of aligned bonds along a bond line 27 may fall on the bond line 27, while the first side portions 35 of un-aligned bonds along the bond line 27 are spaced from the bond line 27. For instance, some of the un-aligned bonds may be located proximate the bond line 27 with the first side portion 35 spaced from the bond line 27 and the un-aligned bonds do not overlap the bond line 27. In other examples, the un-aligned bonds may be located proximate the bond line 27 with the first side portion 35 spaced from the bond line 27 and the un-aligned bonds do overlap the bond line 27. Accordingly, it should be understood that perfect alignment of all of the bonds 20 along bond lines 27 is not needed to remain within the scope of this disclosure.

As mentioned, in at least some embodiments, such as the embodiment of FIGS. 1-3A-C, the first side portions 35 of the bonds 20 (and/or the bond lines 27) may form an angle 40 with respect to the elastomeric strands 16 (and more specifically, the lateral axis 28 of the elastomeric strands 16).

In such embodiments, the angle 40 may range anywhere between about 0 degrees and about 180 degrees. In some more specific embodiments, the angle 40 may range between about 15 degrees and about 90 degrees, or between about 30 degrees and about 89 degrees, or between about 50 degrees and about 88 degrees. In other embodiments, the angle 40 may range between about 105 degrees and about 180 degrees, or between about 120 degrees and about 179 degrees, or between about 140 degrees and about 178 degrees.

It should be appreciated that the specific angle 40 chosen will affect the particular stretch properties of the elasticated material 10. One particular stretch property is the amount of elongation of the elasticated material 10 in the longitudinal direction 31 at a given force which is applied in the longitudinal direction 31. In this example, where the angle 40 is close to 90 degrees, such as between about 80 degrees and about 100 degrees, the elasticated material 10 will elongate a relatively little amount in the longitudinal direction 31. This is because the bonds 20 will extend in relatively longitudinally-oriented lines in such embodiments, thereby resisting the longitudinally-applied force and preventing elongation of the material in the longitudinal direction 31. However, where the angle 40 is not close to 90 degrees, for instance less than about 80 degrees or greater than about 100 degrees, the elasticated material 10 will elongate a relatively greater amount in the longitudinal direction 31 under the given longitudinally applied force. This is due to the fact that as the angle 40 deviates from 90 degrees, the bonds 20 will extend in lines that extend less in the longitudinal direction 31. In such embodiments, the bonds 20 are less aligned to resist the given force applied in the longitudinal direction 31, resulting in greater longitudinal elongation of the elasticated material 10 in the longitudinal direction 31.

Figure 4:
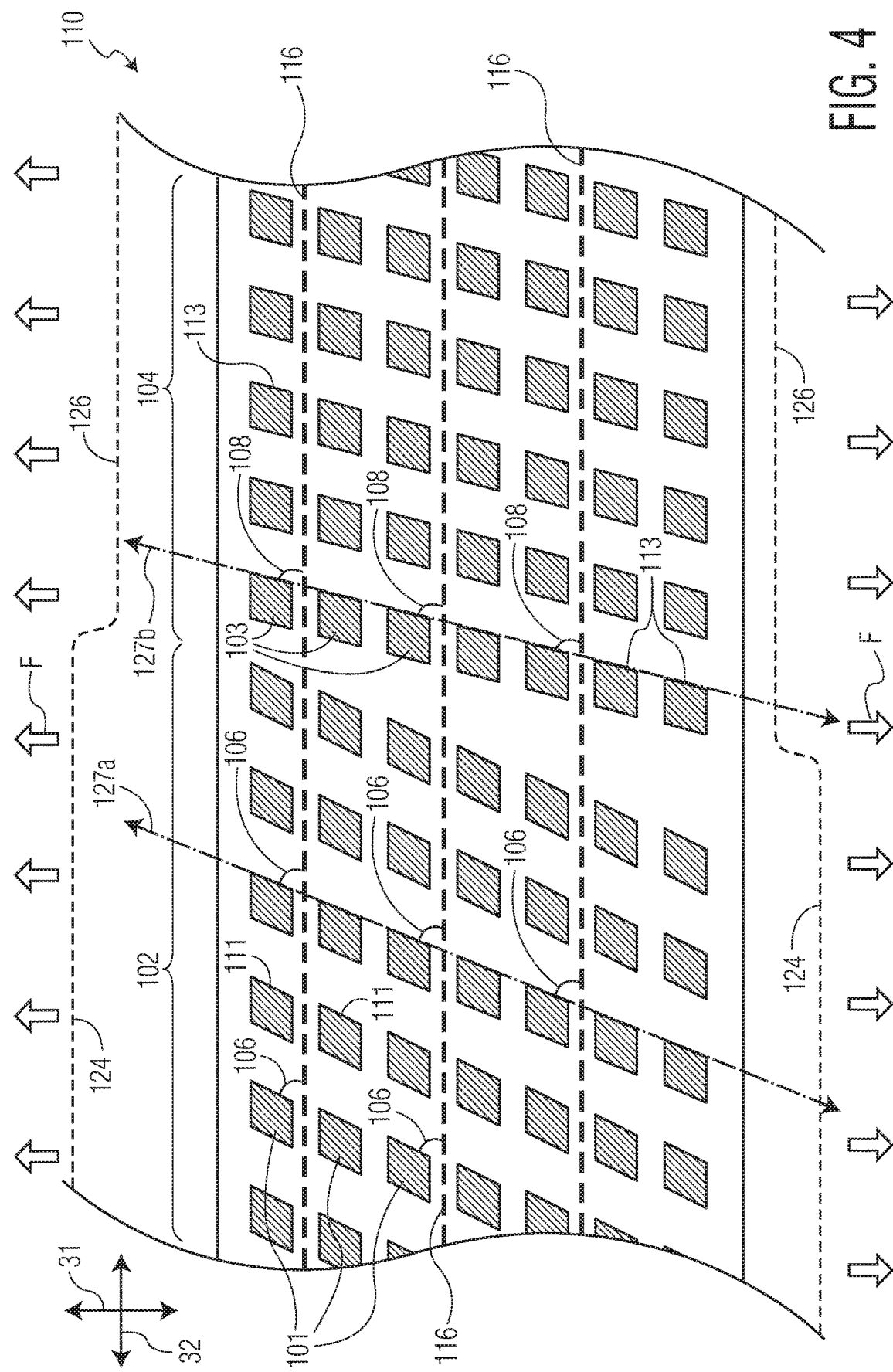
FIG. 4 is a plan view of a stretched elasticated material including multiple bonds having different angles with respect to the elastomeric strands of the elasticated material, according to aspects of the present disclosure.

In the examples of FIGS. 1-3A-C, this particular stretch property may be the same along the length of the elasticated material 10, as the specific configuration of the strands 16, the first and second layers of material 12, 14, and the bonds 20, including the angle 40, do not differ within different regions of the material 10. In contrast, FIGS. 4-6, 8, 10, and 13-15 depict further embodiments of elasticated materials according to the present disclosure, including elasticated materials that have differing stretch properties along their length. Specifically, FIG. 4 is a plan view of an exemplary elasticated material 110 in a stretched state—where the elasticated material 110 has been stretched in the lateral direction 32 such that there are no peaks or valleys present in the depiction of the elasticated material 110 in FIG. 4.

In general, the elasticated material 110 of FIG. 4 may be similar to the elasticated material 10 described with respect to FIGS. 1-3A-C. However, unlike the elasticated material 10, the elasticated material 110 may have a first region 102 including bonds 101 which have first side portions 111 forming angles 106 with respect to the laterally extending elastomeric strands 116. The elasticated material 110 may additionally have a second region 104 including bonds 103 which have first side portions 113 forming angles 108 with respect to the laterally extending elastomeric strands 116.

In some embodiments, the bonds 101 and the bonds 103 may be similar except for the differently angled first side portions 111, 113 and/or or the bonds 101, 103 may be aligned along differently angled bond lines 127a, 127b as shown in FIG. 4. As can be seen, the first side portions 111 of the bonds 101 (and/or the bond lines 127a) may form a first angle 106 with respect to the laterally extending elastomeric strands 116, while the first side portions 113 of the bonds 103 (and/or the bond lines 127b) may form a second angle 108 with respect to the laterally extending elastomeric strands 116.

Additionally, or alternatively, in some embodiments, the bonds 101, 103 may be longitudinally and laterally aligned as shown in FIG. 4. That is, the bonds 101, 103 may have the same longitudinal spacing and the same lateral spacing both within each set of bonds 101, 103 and between the sets of bonds 101, 103. However, in other embodiments, the longitudinal and/or lateral spacing of the bonds 101, 103 may vary between the sets of bonds 101, 103 and/or within each set of bonds 101, 103. For instance, at least some longitudinally adjacent bonds within the sets of bonds 101 and/or 103 may have greater longitudinal spacing where elastomeric strands do not pass between the longitudinally adjacent bonds than the longitudinal spacing of longitudinally adjacent bonds where an elastomeric strand does pass between the longitudinally adjacent bonds.

In different embodiments, the angles 106, 108 may range anywhere between about 0 degrees and about 180 degrees. In some more specific embodiments, the angles 106, 108 may range between about 15 degrees and about 90 degrees, or between about 30 degrees and about 89 degrees, or between about 50 degrees and about 88 degrees. In other embodiments, the angles 106, 108 may range between about 105 degrees and about 180 degrees, or between about 120 degrees and about 179 degrees, or between about 140 degrees ad about 178 degrees. Additionally, the angles 106, 108 are different, and in at least some embodiments, one of the angles 106, 108 is less than 90 degrees while the other of the angles 106, 108 is greater than 90 degrees.

As should be appreciated, this difference in the angles 106, 108 results in the elasticated material 110 having different stretch properties along is lateral length. For instance in the example of FIG. 4, the first region 102 may elongate in the longitudinal direction 31 a first amount under a given force applied in the longitudinal direction 31—the given force being indicated by arrows F. The relative amount of elongation of the first region 102 under the applied force is represented by the dashed outline 124 of the elasticated material 110 in the first region 102. In the second region 104, however, the elasticated material 110 may not elongate as much in the longitudinal direction 31 under the same applied force due to the differently angled first side portions 113 of the bonds 103 (and/or the differently angled bond lines 127b) which are angled closer to 90 degrees than the first side portions 111 of the bonds 101 (and/or the angled bond lines 127a). The relative amount of elongation of the second region 104 is represented by the dashed outline 126 of the elasticated material 110 in the second region 104. As can be seen, the relative elongation of the first region 102 is greater than the relative elongation of the second region 104.

Figure 5:
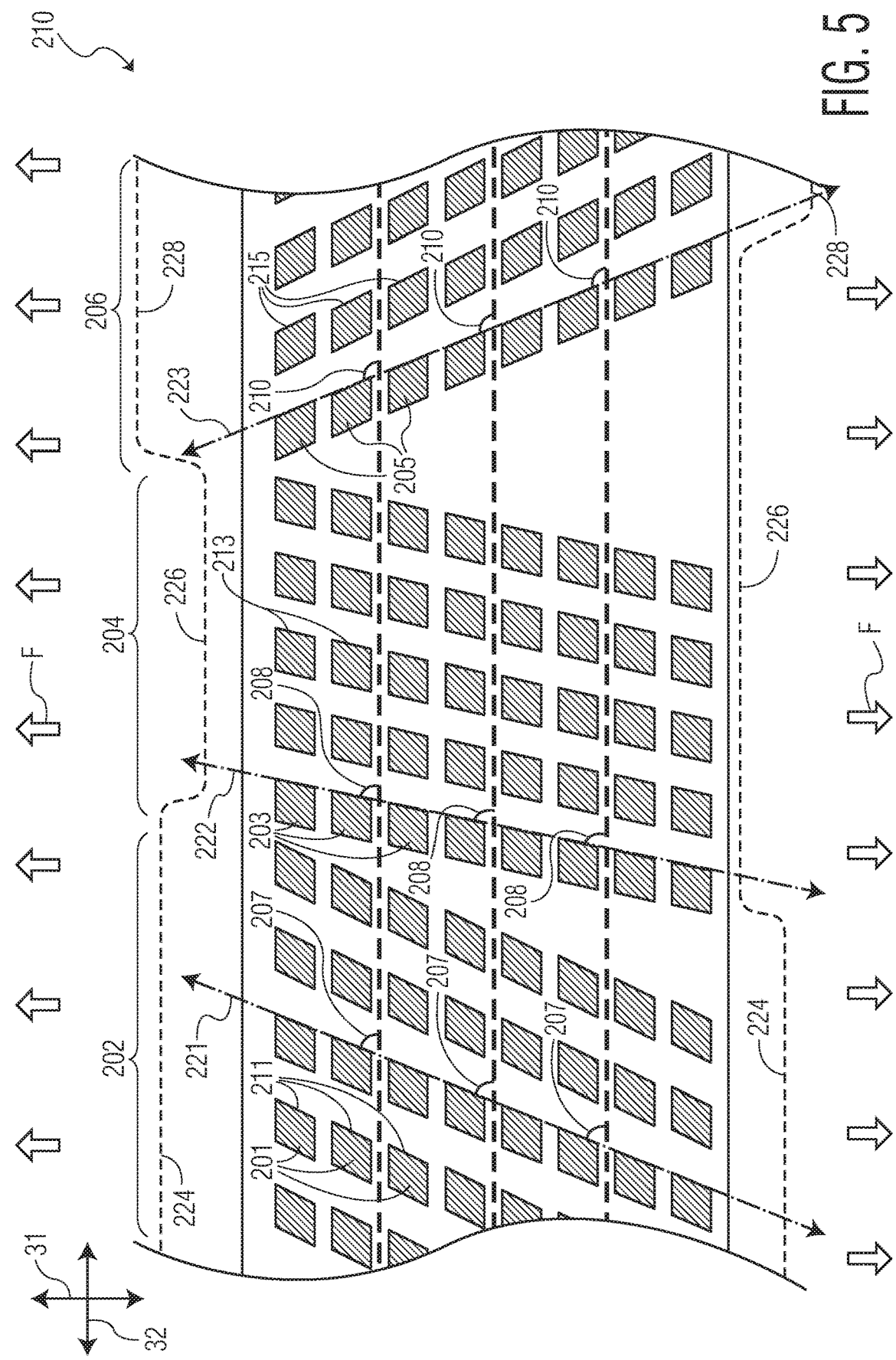
FIG. 5 is a plan view of another stretched elasticated material including multiple bonds having different angles with respect to the elastomeric strands of the elasticated material, according to aspects of the present disclosure

FIG. 5 depicts exemplary elasticated material 210 in a plan view and in a stretched state—where the elasticated material 210 has been stretched in the lateral direction 32 such that there are no peaks or valleys present. In general, the elasticated material 210 of FIG. 5 may be similar to the elasticated material 10 described with respect to FIGS. 1-3A-C, and the elasticated material 110 described with respect to FIG. 4. However, unlike the elasticated material 110, the elasticated material 210 may contain not only a first region 202 and a second region 204, but the elasticated material 210 also includes a third region 206.

As with the elasticated material 110, the first region 202 of the elasticated material 210 includes bonds 201 having first side portions 211 which form an angle 207 with respect to the elastomeric strands 216, and the second region 204 of the elasticated material 210 includes bonds 203 having first side portions 213 which form an angle 208 with respect to the elastomeric strands 216. Additionally, the third region 206 of the elasticated material 210 includes bonds 205 having first side portions 215 which form an angle 210 with respect to the elastomeric strands 216.

Again, in another way of describing the elasticated material 210, longitudinally adjacent bonds of the bonds 201, 203, and/or 205 may extend longitudinally down the elasticated material 210 in bond lines, such as bond lines 221, 222, and 223. In the embodiment of FIG. 5, not only do the first side portions 211, 213, and 215 of the bonds 201, 203, and 205 form angles 207, 208, and 210, respectively, with respect to the elastomeric strands 216, each of the bond lines 221, 222, and 223 form the angles 207, 208, and 210, respectively, with respect to the elastomeric strands 216 as well.

In different embodiments, the angles 207, 208 and 210 may range anywhere between about 0 degrees and about 180 degrees. In some more specific embodiments, the angles 207, 208 and 210 may range between about 15 degrees and about 90 degrees, or between about 30 degrees and about 89 degrees, or between about 50 degrees and about 88 degrees. In other embodiments, the angles 207, 208 and 210 may range between about 105 degrees and about 180 degrees, or between about 120 degrees and about 179 degrees, or between about 140 degrees ad about 178 degrees. Additionally, each of the angles 207, 208 and 210 are shown as different, and in at least some embodiments, one of the angles 207, 208 and 210 is less than 90 degrees while another of the angles 207, 208 and 210 is greater than 90 degrees. In other embodiments, two of the angles 207, 208, and 210 may be less than 90 degrees while the third of the angles 207, 208, and 210 may be greater than 90 degrees. Alternatively, at least one of the angles 207, 208, and 210 may be greater than 90 degrees while at least another of the angles 207, 208, and 210 is less than 90 degrees, and in further embodiments, two of the angles 207, 208 and 210 may be greater than 90 degrees while the third of the angles 207, 208, and 210 may be less than 90 degrees. In still further embodiments, at least one of the angles 207, 208, and 210 may be equal to 90 degrees while the other two of the angles 207, 208, and 210 may be less than 90 degrees, greater than 90 degrees, or a first of the other two of the angles 207, 208, and 210 may be less than 90 degrees while a second of the other two of the angles 207, 208, and 210 may be greater than 90 degrees.

As should be appreciated, this difference in the angles 207, 208 and 210 results in the elasticated material 210 having different stretch properties along is lateral length. For instance in the example of FIG. 5, the first region 202 may elongate in the longitudinal direction 31 a first amount under a given force applied in the longitudinal direction 31—the given force being indicated by arrows F. The relative amount of elongation of the first region 202 under the given applied force is represented by the dashed outline 224 of the elasticated material 210 in the first region 202. In the second region 204, however, the elasticated material 210 may not elongate as much in the longitudinal direction 31 under the given applied force F due to the differently angled first side portions 213 of the bonds 203 (or, the differently angled bond lines 222) which are angled closer to 90 degrees than the first side portions 211 of the bonds 201 (or, the angled bond lines 221). The relative amount of elongation of the second region 204 is represented by the dashed outline 226 of the elasticated material 210 in the second region 204. As can be seen, the relative elongation of the first region 202 is greater than the relative elongation of the second region 204.

Additionally, the third region 206 may elongate in the longitudinal direction 31 under the given applied force F yet a relatively greater amount than either of the first region 202 or the second region 204, as represented by dashed outline 228. For instance, the first side portions 215 of the bonds 205 in the third region 206 are angled with respect to the elastomeric strands 216 away from 90 degrees a greater amount than either of the first side portions 211, 213 of the bonds 201, 203 (or, the bond lines 221, 222) within the regions 202 and 204 are angled away from 90 degrees. Accordingly, the longitudinal alignment of the bonds 205 in the third region 206 is relatively less than the longitudinal alignment of the bonds 201, 203 in the first region 202 and the second region 204 and therefore resists the longitudinally-applied given force F less than the bonds 201, 203 of the first region 202 and the second region 204.

It should be understood that the embodiment of FIG. 5 is just one contemplated embodiment where an elasticated material, e.g. elasticated material 210, has at least three different regions having three different stretch properties along its length. In other contemplated embodiments, the particular order of the differing angles of the first side portions 211, 213, and 215, or the bond lines 221, 222, and 223, with respect to the elastomeric strands 16 may be different than shown in FIG. 5. Additionally, other contemplated embodiments may have all of the different angles be less than 90 degrees, or greater than 90 degrees.

Figure 6:
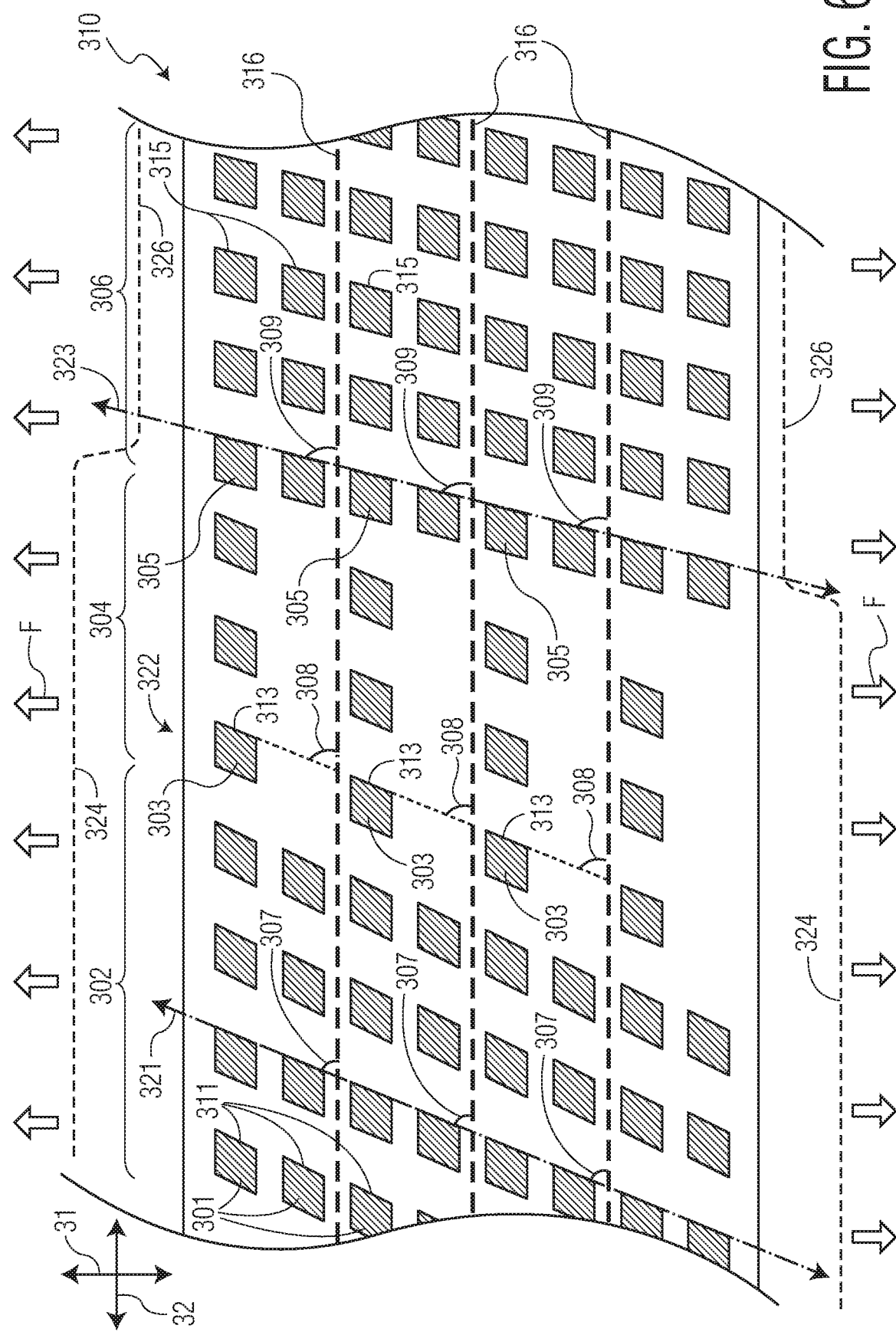
FIG. 6 is a plan view of yet another stretched elasticated material including multiple bonds having different angles with respect to the elastomeric strands of the elasticated material and regions with bonds having different longitudinal spacing, according to aspects of the present disclosure

FIG. 6 depicts exemplary elasticated material 310 in a plan view and in a stretched state—where the elasticated material 310 has been stretched in the lateral direction 32 such that there are no peaks or valleys present in the elasticated material 310. In general, the elasticated material 310 of FIG. 6 may be similar to the elasticated material 210 described with respect to FIG. 5. However, instead of having three different regions comprising bonds having first side portions, or bond lines, which form differing angles with respect to elastomeric strands, the elasticated material of FIG. 6 has at least two regions comprising bonds having first side portions, or bond lines, which form differing angles with respect to elastomeric strands, and a region where none of the elastomeric strands include entrapped portions.

In the embodiment of FIG. 6, the elasticated material 310 comprises region 302 comprising bonds 301 having first side portions 311, or bond lines 321, which form an angle 307 with respect to the elastomeric strands 316. Additionally, the elasticated material 310 further includes region 306 comprising bonds 305 having first side portions 315, or bond lines 322, which form an angle 309 with respect to the elastomeric strands 316. The angle 316 is different than the angle 311 in at least some embodiments. Elasticated material 310 further includes region 304 comprising bonds 303. As can be seen in FIG. 6, the bonds 303 of region 304 may have different longitudinal spacing than bonds 301 and/or bonds 305. For instance, at least one pair longitudinally adjacent bonds 303 within region 304 that are disposed on opposite sides of one of the elastomeric strands 316 may be longitudinally spaced a distance that is greater than or equal to the un-tensioned diameter of the elastomeric strand 316. In some embodiments, as is shown in FIG. 6, all pairs of longitudinally adjacent bonds 303 within region 304 that are disposed on opposite sides of elastomeric strands 316 may be longitudinally spaced a distance greater than or equal to the un-tensioned diameter of the elastomeric strands 316. Providing regions such as region 304 where the elastic strands 16 are not entrapped may be beneficial where regions of a material are to be de-elasticized. In such materials, the elastic strands 16 may be severed at only one point within the region where the elastic strands 16 are not entrapped, such as region 304, in order to de-elasticize the entire region 304. Of course, the elastic strands 16 could be severed at multiple points within the region 304, which may better de-elasticize the region 304. As one example, it is sometimes beneficial to de-elasticize a region of an elasticated material which spans across an absorbent core of an absorbent article.

Accordingly, at least one of the elastomeric strands 316 within the region 304 may not include any entrapped portions, due to the different longitudinal spacing of the bonds 303 within the region 304. In some embodiments, all of the elastomeric strands within region 304 may not include any entrapped portions, while in other embodiments, at least some of the elastomeric strands 16 within region 304 may still include entrapped portions, as they do in regions 301, 305.

Further, in some embodiments, the lateral first portions 313 of the bonds 303, or the bond lines 323, in region 304 may form an angle 308 with respect to the elastomeric strands 316, and this angle may be the same as either angle 307 or 309. In other embodiments, however, angle 308 may be different than both of angle 307 and 309. Where angle 308 is the same as either angle 307 or 309, region 304 may elongate in the longitudinal direction 31 under a given force applied in the longitudinal direction 31, indicated by arrows F, the same amount as either region 302 or region 306. The relative elongation of the different regions 302, 304, and 306 in FIG. 6 is indicated by dashed outlines 324 and 326. However, in other embodiments, e.g. where angle 308 is different than both of angles 307 and 309, region 304 may elongate in the longitudinal direction 31 under the given force applied in the longitudinal direction 31 a different amount than either of region 302 and region 306.

Of course, any of the above described elasticated materials may be used within various different clothing garments and absorbent articles. For instance, the disclosed elasticated materials may form at least a portion of a waistband of a clothing garment or absorbent article, or at least a portion of elastic leg cuffs of a clothing garment or absorbent article, or may be used within other portions of absorbent articles such as within an absorbent core of an absorbent article, as part of a containment flap of an absorbent article, or as part of a surge and/or distribution layer of an absorbent article. FIG. 7 depicts exemplary absorbent article 400 which includes elasticated materials as part of its waistbands and leg cuffs.

The embodiment of FIG. 7 illustrates absorbent article 400 which comprises an absorbent article manufactured in what is commonly termed a cross-machine direction (CD) process. However, it should be understood that other absorbent articles which are manufactured in machine-direction (MD) processes may contain elasticated materials according to the present disclosure without departing from the spirit and scope of the disclosure.

The absorbent article 400 can comprise a three-piece construction where the absorbent article 400 has a chassis 406 including a front waist panel 402 having a front waist edge 401, a rear waist panel 404 having a rear waist edge 403, and an absorbent panel 409 extending between the front waist panel 402 and the rear waist panel 404. The absorbent panel 409 may generally include absorbent body 408. In some embodiments, the absorbent panel 409 can have a first lateral side edge 405 and a second lateral side edge 407 and can overlap the front waist panel 402 and the rear waist panel 404. The absorbent panel 409 can be bonded to the front waist panel 402 and the rear waist panel 404 to define a three-piece construction. However, it is contemplated that an absorbent article can be manufactured in a CD process without being a three-piece construction garment, which is also sometimes referred to as a one-piece construction (not shown), as the front waist panel 402 and the rear waist panel 404 are integral with one another by way of commonly connected components forming the waist panel such as a bodyside liner and/or an outer cover which can envelope the absorbent panel 409 or simply cover the garment side of the absorbent panel 409.

The front waist panel 402 and the rear waist panel 404 may generally comprise elastomeric strands 416 disposed between at least two layers of material. For instance, the front waist panel 402 and the rear waist panel 404 may comprise an elasticated material as described herein. In at least some embodiments, the front waist panel 402 and/or the rear waist panel 404 may have a central region 421, and side edge regions 422, 423. The central region 421 may be formed to have a first amount of elongation in the longitudinal direction 31 under a given longitudinally-applied force, while the side edge regions 422, 423 may be formed to have second amounts of elongation in the longitudinal direction 31 under the given longitudinally-applied force. The side edge regions 422, 423 may even be formed to have different amounts of elongation from each other. Other contemplated embodiments include additional side edge regions, for instance, four, six, or eight side edge regions formed to have differing amounts of elongation. This feature of the front waist panel 402 and/or the rear waist panel 404 may allow for better fit between the absorbent article 400 and a wearer. For instance, the side edge regions 422, 423 may have a greater amount elongation in the longitudinal direction 31 under a longitudinally-applied force than the central region 421 in some embodiments, or a lesser amount elongation in the longitudinal direction 31 under a longitudinally-applied force than the central region 421 in other embodiments. These different embodiments may impart different beneficial fit properties to the absorbent article 400.

FIG. 8 depicts a close-up of box 431 of FIG. 7 detailing more specifically the different structure of the front waist panel 402 in the regions 421, 423. As can be seen, the front waist panel 402 contains bonds 420 and bonds 430, oriented in bond lines 425 and 427, respectively. As can be seen, the first side portions 426, or the bonds lines 425, of the bonds 420 may be angled differently with respect to the elastomeric strands 416 than the first side portions 428, or the bond lines 427, of bonds 430. For instance, the first side portions 426 of the bonds 420, which reside in the region 421, may form a first angle 424 with respect to the elastomeric strands 416, while the first side portions 428 of the bonds 430, which reside in the region 423, may form a second angle 429 with respect to the elastomeric strands 416. The first angle and the second angle are different. Accordingly, the front waist panel 402 may exhibit different longitudinal elongation under a given longitudinally-applied force in the different regions 421, 423.

Figure 9:
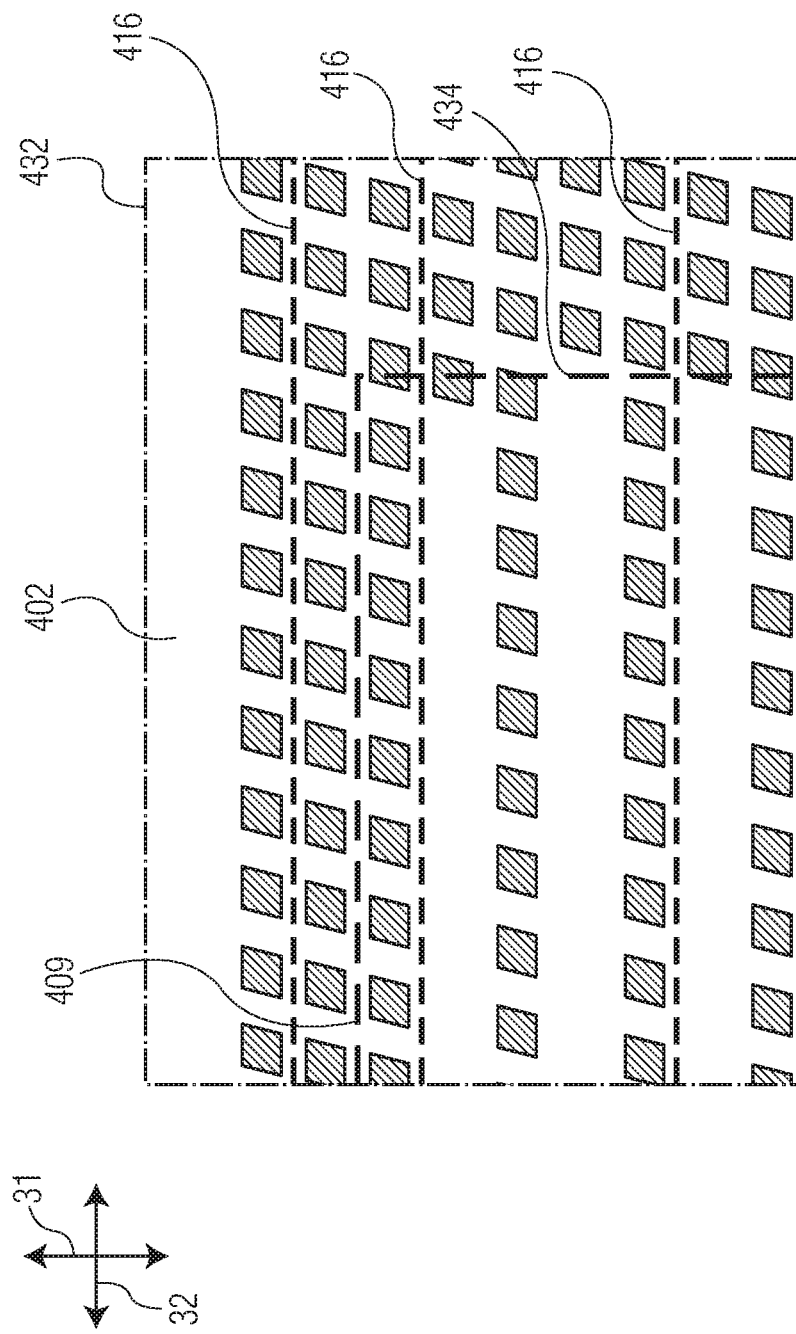
FIG. 9 is a plan view of another exemplary elasticated material that may comprise a portion of a waistband of the absorbent article of FIG. 7.

In some additional or alternative embodiments, the front waist panel 402 and/or the rear waist panel 404 may have overlap regions where the absorbent panel 409 overlaps the front waist panel 402 and/or the rear waist panel 404, such as overlap region 434 shown in FIG. 9. In at least some of these embodiments, the portions of the elastomeric strands 416 that cross through these overlap regions may not have entrapped portions.

FIG. 9 depicts a close-up of box 432 detailing the specific structure of the front waist panel 402 including overlap region 434 where the absorbent panel 409 overlaps the front waist panel 402. As can be seen, the bonds 420 of the front waist panel 402 within the overlap region 434 are spaced apart in the longitudinal direction 31 differently than the bonds 420 outside of the overlap region 434. For instance, the bonds 420 outside of the overlap region 434, or at least the bonds 420 outside of the overlap region 434 that are longitudinally adjacent and for which an elastomeric strand 416 is positioned therebetween, may be spaced apart longitudinally a distance less than the un-tensioned diameter of the elastomeric strands 416. Accordingly, outside of the overlap region 434, the elastomeric strands 416 may have entrapped portions where the elastomeric strands 416 pass between the bonds 420. The bonds 420 inside of the overlap region 434, or at least longitudinally adjacent bonds 420 within the overlap region 434 for which an elastomeric strand 416 is positioned therebetween, may be spaced apart longitudinally a distance greater than or equal to the un-tensioned diameter of the elastomeric strand 416. Accordingly, the elastomeric strands 416 within the overlap region 434 may have some portions which pass between bonds 420 and which are not entrapped by the bonds 420.

Of course, it should be understood that the overlap region 434, which describes where the absorbent panel 409 overlaps the front waist panel 402, is only one exemplary boundary of where the bonds 420 may have different longitudinal spacing. For instance, in some embodiments, the bonds 420 may have longitudinal spacing that is greater than the un-tensioned diameter of the elastomeric strands 16 where the bonds 420 overlap the absorbent body 408 as opposed to the entire absorbent panel 409.

In some additional or alternative embodiments, the absorbent article 400 may include elasticated leg cuffs 410, 411 which have differential elongation properties along their length. For instance, it may be beneficial for the elasticated leg cuffs 410, 411 to have greater elongation in the lateral direction 32 in regions closer to the front waist panel 402 and/or the rear waist panel 404 to improve fit of the absorbent article 400.

Figure 10:
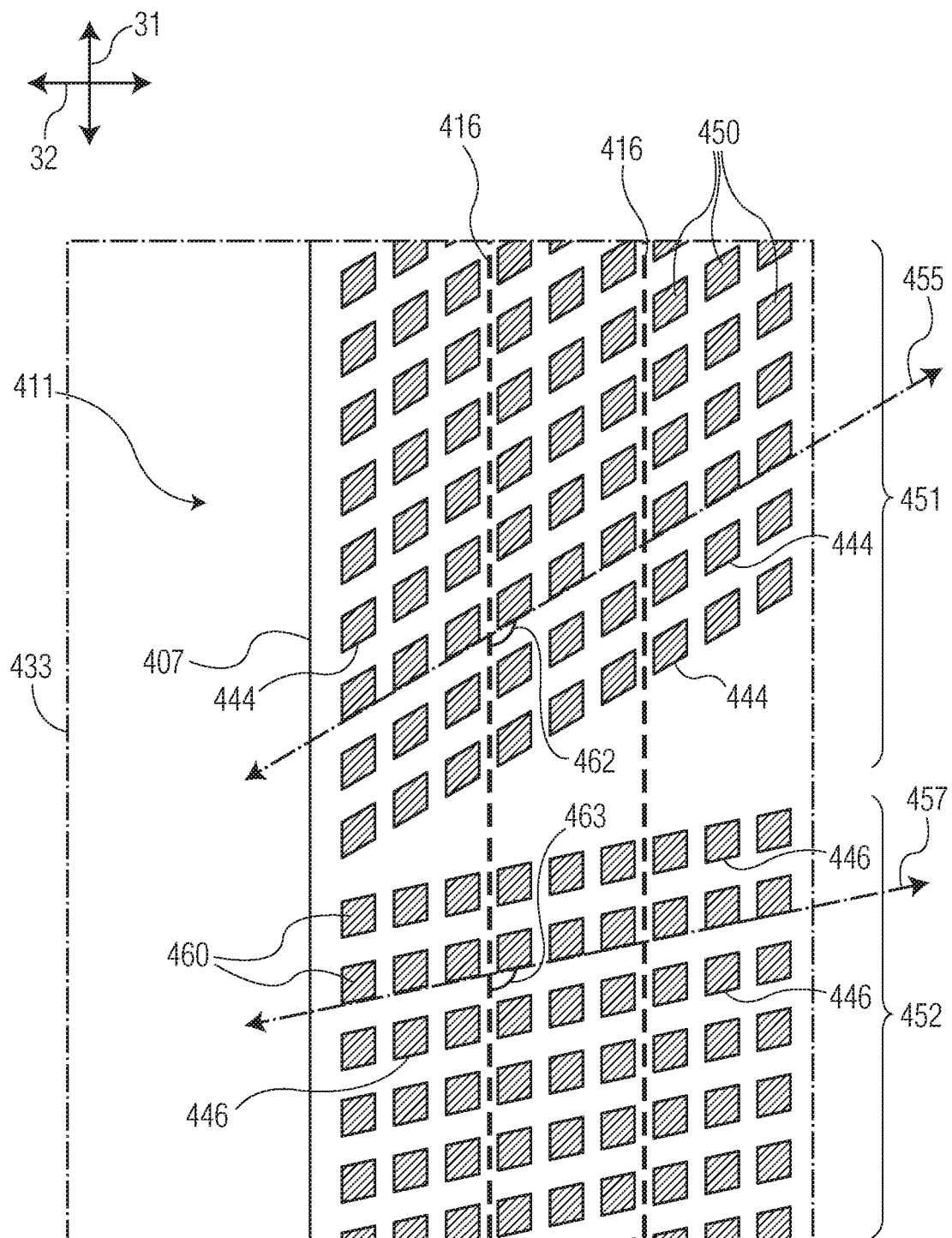
FIG. 10 is a plan view of an exemplary elasticated material that may comprise a portion of a leg cuff of the absorbent article of FIG. 7.

FIG. 10 depicts a close-up of box 433 of FIG. 7 detailing more specifically the different structure of the elasticated leg cuffs 410, 411. As can be seen in FIG. 10, elastomeric strands 416, which represent leg elastomeric strands in the portion of the article 400 highlighted by box 433, are shown running in the longitudinal direction 31 through regions 451 and 452.

The regions 451 and 452 include bonds 450 and 460 arranged in bond lines 455 and 457, respectively, which have first side portions 444 and 446. The first side portions 444 of the bonds 450, and the bond lines 455, may form a first angle with respect to the elastomeric strands 416, while the first side portions 446 of the bonds 460, and the bond lines 457, may form a second, different angle with respect to the elastomeric strands 416. Accordingly, the elastic leg cuff 411 may exhibit different lateral elongation under a given laterally-applied force in the different regions 451, 452. This may be beneficial to allow for more form fitting of the leg cuffs 410, 411 around an upper thigh and buttock region of a wearer.

Other exemplary absorbent articles of the present disclosure may include waist panels and leg cuffs which have different stretch properties. For instance, instead of the stretch properties of the waist panels or leg cuffs varying within the waist panels or leg cuffs, the stretch properties may be different between the waist panel and the leg cuffs.

Figure 11:
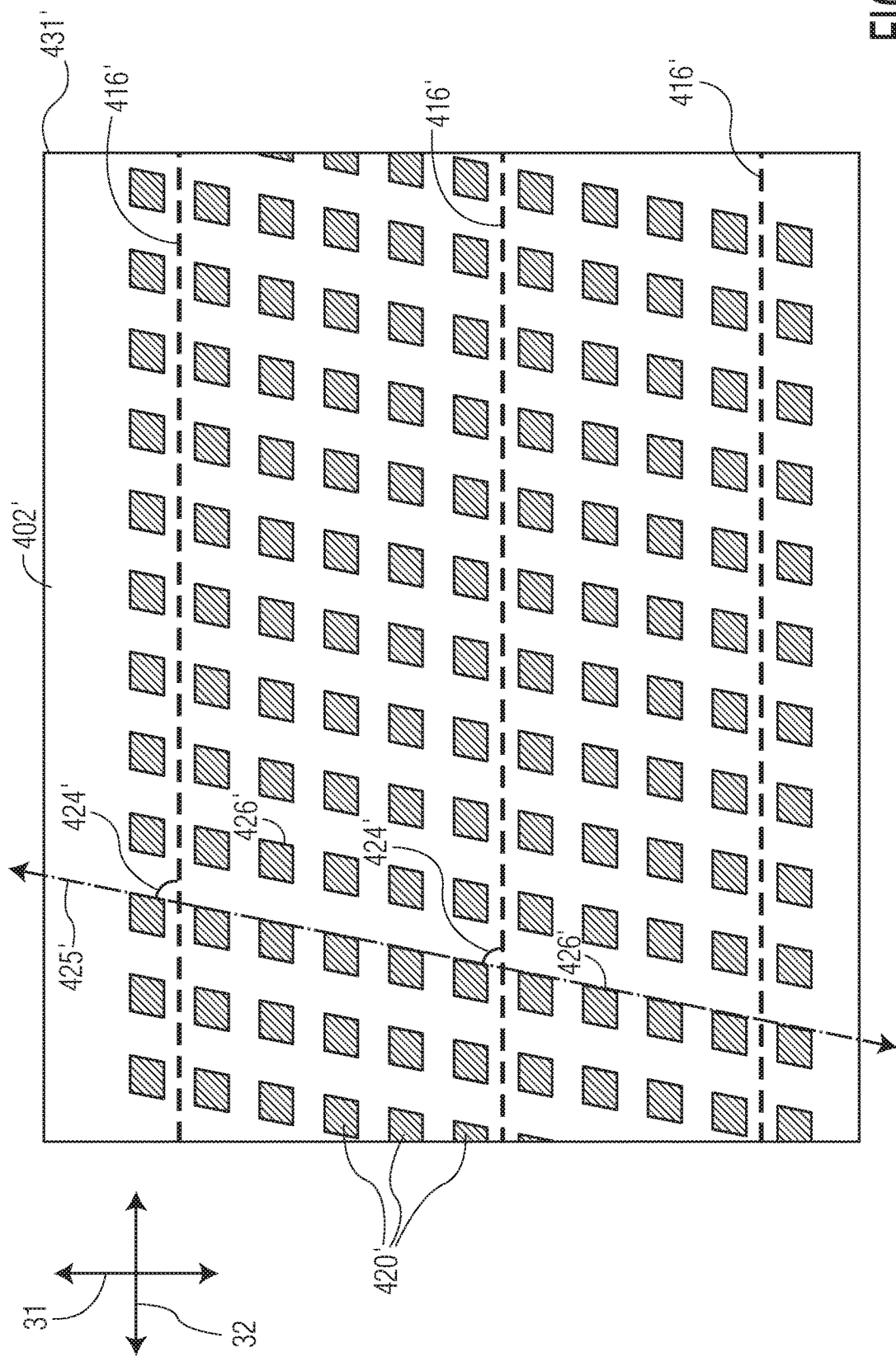
FIG. 11 is a plan view of another stretched elasticated material including multiple bonds having different angles with respect to the elastomeric strands of the elasticated material, according to aspects of the present disclosure.
Figure 12:
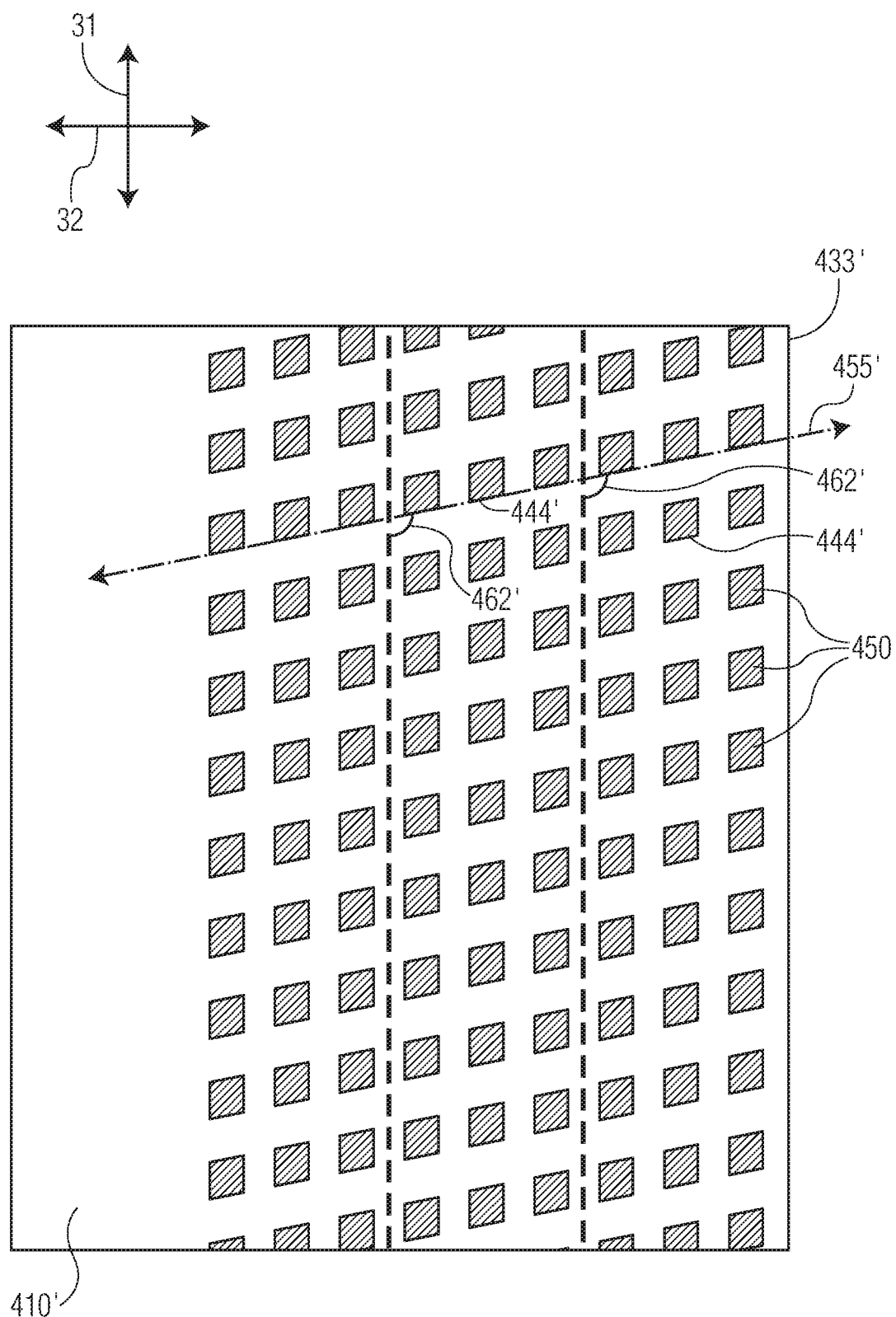
FIG. 12 is a plan view of yet another stretched elasticated material including multiple bonds having different angles with respect to the elastomeric strands of the elasticated material, according to aspects of the present disclosure.

FIG. 11 depicts a close-up of box 431 of FIG. 7, labeled as box 431' in FIG. 11, detailing the structure of the front waist panel 402 of FIG. 7, labeled as 402' in FIG. 11. As can be seen, the front waist panel 402' contains bonds 420', oriented in bond lines 425'. The first side portions 426', or the bonds lines 425', of the bonds 420' may be angled at a first angle 424' with respect to the elastomeric strands 416. FIG. 12 depicts a close-up of box 433 of FIG. 7, labeled as box 433' in FIG. 12, detailing the structure of the elasticated leg cuff 410, labeled as 410' in FIG. 12. As can be seen, the leg cuff 410' contains bonds 450', oriented in bond lines 455'. The first side portions 444', or the bonds lines 455', of the bonds 450' may be angled at a second angle 462' with respect to the elastomeric strands 416. The first angle 424' and the second angle 462' are different in these embodiments in order to provide the different desired stretch properties at the different locations of the absorbent article, resulting in an article with better fit.

Other contemplated embodiments include materials and absorbent articles and clothing garments having materials which have symmetric stretch properties and/or continuous stretch properties. For instance, it may be beneficial to provide materials or use materials within absorbent articles or clothing garments that stretch a same amount under given forces applied in differing directions and/or have stretch in all directions. In some embodiments, this may be achieved by varying the angles at which the bonds of the material are oriented with respect to elastic strands between different elastic strands.

Figure 13:
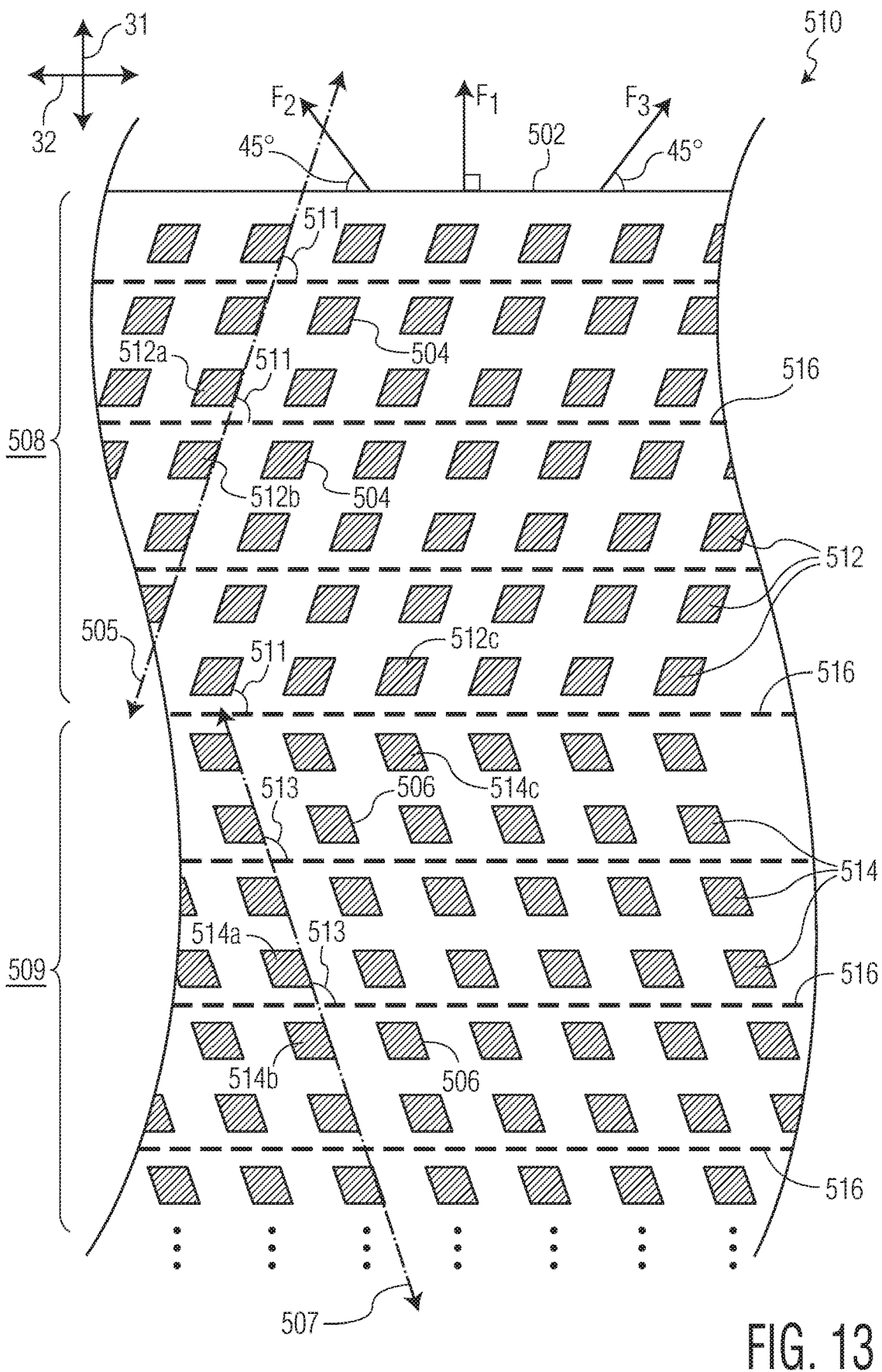
FIG. 13 is a plan view of still another stretched elasticated material including multiple bonds having different angles with respect to the elastomeric strands of the elasticated material, according to aspects of the present disclosure.

FIG. 13 depicts an exemplary material 510 which may be used in absorbent articles or clothing garments which has a symmetrical stretch property. In the example of FIG. 13, the material 510 has a top edge 502 and two sets of bonds 512, 514 which have side portions 504, 506, respectively, which are angled differently from each other with respect to the elastomeric strands 516. Of course, as described with respect to other materials of the present disclosure, the bonds 512, 514 of the material 510 could be oriented in bond lines 505, 507, respectively, which form different angles with respect to the elastomeric strands 516. For instance, the side portions 504 of the bonds 512, or the bond lines 505, may form a first angle 511 with respect to the elastomeric strands 516, such as shown in region 508 of the material 510. The side portions of the bonds 514, or the bond lines 507, may form a second angle 513 with respect to the elastomeric strands 516 which is different than the first angle 511, such as shown in region 509 of the material 510.

In general, the bonds 512, 514 of the material 510 may have lateral and longitudinal spacing that is similar to the lateral and longitudinal spacing described with respect to the bonds of the other elasticated materials of the present disclosure. For instance, the bonds 512, 514 between which an elastomeric strand 516 extends may have a longitudinal spacing that is less than the un-tensioned diameter of the elastomeric strand 516. The longitudinally adjacent bonds 512, 514 between which an elastomeric strand 516 does not extend may have any of a variety of different longitudinal spacings, including a spacing which is greater than an un-tensioned diameter of the elastomeric strands 516, as described with respect to other elasticated materials of the present disclosure. Also, the lateral spacing between laterally adjacent bonds 512, 514 may be any of the options described with respect to other elasticated materials of the present disclosure.

Looking at FIG. 13 more specifically, region 508 includes bonds 512 which have first side portions 504 which form an angle 511 with respect to the elastomeric strands 516. In at least some portions of region 508, longitudinally adjacent bonds between which an elastomeric strand 516 extends may entrap the elastomeric strand 516. Such longitudinally adjacent bonds, for example bonds 512a, 512b, may be spaced in the longitudinal direction 31 less than the un-tensioned diameter of the elastomeric strand 516 to entrap the elastomeric strand 516. The region 509 includes bonds 514 which have first side portions 506 which form an angle 513 with respect to the elastomeric strands 516. Additionally, in at least some portions of region 509, longitudinally adjacent bonds between which an elastomeric strand 516 extends may entrap the elastomeric strand 516. Such longitudinally adjacent bonds, for example bonds 514a, 514b, may be spaced in the longitudinal direction 31 less than the un-tensioned diameter of the elastomeric strand 516 to entrap the elastomeric strand 516. As can be seen, unlike elasticated material 110 of FIG. 4, the elastomeric strand 516 extending between the bonds 512a, 512b is different than the elastomeric strand 516 which extends between bonds the 514a, 514b. Accordingly in the embodiment of FIG. 13, the bonds of the elasticated material 510 which form different angles with respect to elastomeric strands, such as different angles 511, 513, are disposed about different ones of the elastomeric strands 516 of the material 510.

Further, in some embodiments, an elastomeric strand 516 may extend between the two regions 508, 509. In such embodiments, the elastomeric strand 516 may separate one of the bonds 512, for example 512c which is part of the region 508, from one of the bonds 514, for example 514c which is part of the region 509. The bonds 512c, 514c may be spaced apart longitudinally less than an un-tensioned diameter of the elastomeric strand 516 to entrap the elastomeric strand 516. Additionally, the bond 512c may form the angle 511 with respect to the elastomeric strand 516 (or a line parallel to the elastomeric strand 516), while the bond 514c forms the angle 513 with respect to the elastomeric strand 516 (or a line parallel to the elastomeric strand 516). However, in other embodiments, it is possible that no elastomeric strand 516 may extend directly between the regions 508, 509.

In general, the angles 511, 513 may have any suitable value, such as between about 15 degrees and about 90 degrees, or between about 30 degrees and about 89 degrees, or between about 50 degrees and about 88 degrees, or between about 105 degrees and about 180 degrees, or between about 120 degrees and about 179 degrees, or between about 140 degrees ad about 178 degrees. In at least some embodiments the angles 511, 513 may differ from 90 degrees by the same amount, except that one of the angles 511, 513 may be less than 90 degrees while the other of the angles 511, 513 may be greater than 90 degrees. For instance, if the angle 511 is 15 degree, 45 degrees, or 75 degrees, the angle 513 may be 105 degrees, 135 degrees, or 165 degrees, respectively. Put another way, the value of the angle 513 in degrees may be 180 minus the value of the angle 511.

The material 510 may have symmetrical stretch properties due to the different regions 508, 509 having bonds with side portions, or forming bond lines, which form different angles with respect to the elastomeric strands 516 of the material 510. The symmetrical stretch property may result from the particular configuration of the angles formed, the longitudinal extent of each of the regions 508, 509, or both. For instance, in some embodiments, the longitudinal extent of each of the regions 508, 509 may be the same. In such embodiments, the angles 511, 513 may also be symmetric about 90 degrees—that is, the angles 511, 513 may differ from 90 degrees by the same amount, except one of the angles 511, 513 is less than 90 degrees, while the other of the angles 511, 513 is greater than 90 degrees. Again, put another way, the value of the angle 513 in degrees may be 180 minus the value of the angle 511. In embodiments where the longitudinal extents of the regions 508, 509 differ, the amount by which the angles 511, 513 vary from 90 degrees may also differ to produce a material that still has symmetrical stretch properties.

The symmetrical stretch properties discussed involve the materials, such as material 510, as having a symmetric amount of stretch in the longitudinal direction 31 under a given applied force in the longitudinal direction 31 when the materials are oriented at angles with respect to the longitudinal direction 31. For instance, the material 510 may stretch a first amount in the longitudinal direction 31 under a given force applied in the longitudinal direction 31, as represented by arrow $F_1$, while the material 510 is oriented perpendicularly with respect to the force $F_1$. Additionally, the material 510 may stretch a second amount in the longitudinal direction 31 under the same given force applied while the material 510 has been rotated some amount with respect to the longitudinal direction 31. For instance, the material 510 may stretch the second amount under the given force, as represented by arrow $F_2$, while the arrow $F_2$ is oriented in the longitudinal direction 31. In this example, the material 510 has been rotated to the right 45 degrees with respect to the longitudinal direction 31. Further, the material 510 may stretch the same second amount in the longitudinal direction 31 under the given force, as represented by arrow $F_3$, while the arrow $F_3$ is oriented in the longitudinal direction 31. In this example, the material 510 has been rotated to the left 45 degrees with respect to the longitudinal direction 31. Accordingly, the material 510 can be seen to have a symmetrical stretch property as the material 510 stretches the same amount under the same force applied at mirrored angles with respect to the longitudinal direction 31, or applied when the material 510 has been rotated an equal amount in either direction with respect to the longitudinal direction 31. This is in contrast to the elasticated materials shown and described in FIGS. 1-6. In those embodiments, the materials exhibit different amounts of stretch under a given force applied at mirrored angles with respect to the longitudinal direction 31, or applied when the materials have been rotated an equal amount in either direction with respect to the longitudinal direction 31.

Materials such as material 510 may also have a continuous stretch property. That is, the material 510 may elongate in the longitudinal direction 31 under a given force applied in the longitudinal direction 31 at every angle the material 510 is rotated with respect to the longitudinal direction 31, even when the layers of material of the material 510 do not have any inherent elastic properties. For instance, as described previously the materials of the present disclosure will resist elongation in a direction that the bonds of the materials align. For instance, the material 10 of FIG. 1 may not elongate at all, or only a small amount such as less than about 1%, where they layers of material of the material 10 do not have any inherent elastic properties under a given force applied in the longitudinal direction 31 when the material 10 is rotated to left with respect to the longitudinal direction 31 by the same number of degrees as is angle 40. This is because in this configuration, the bonds align in the longitudinal direction 31, which is the same direction as the given force, and prevent any elongation of the material 10 in the longitudinal direction 31 at that angle of rotation. Material 510, on the other hand, has no angle of rotation under which the bonds directly align in the longitudinal direction 31. As can be seen, at every angle of rotation of the material 510 with respect to the longitudinal direction 31, some of the bonds 514 and/or 516 will not be aligned in the longitudinal direction 31. Accordingly, the material 510 will exhibit some amount of elongation in the longitudinal direction 31, such as greater than about 1% elongation, at every angle of rotation of the material 510 with respect to the longitudinal direction 31, even where the layers of material of the material 510 have no inherent elastic properties.

Of course, in still further embodiments, elasticated materials according to the present disclosure may features of both exemplary materials 110 and 510. For instance, an exemplary elasticated may have bonds with side portions which form different angles both along a single elastomeric strand and between different elastomeric strands.

Figure 14:
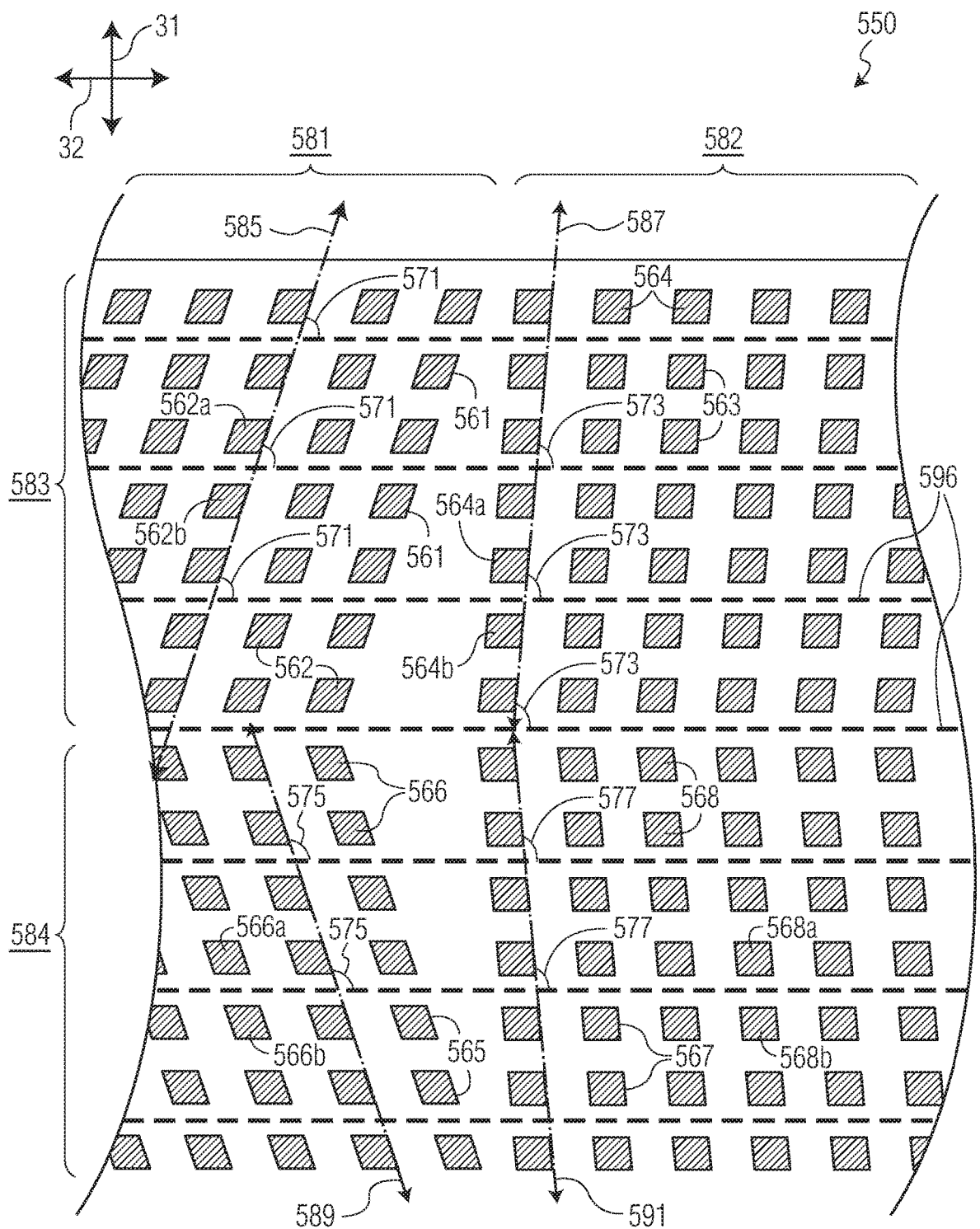
FIG. 14 is a plan view of another exemplary elasticated material that may comprise a portion of a waistband of the absorbent article of FIG. 7.

FIG. 14 depicts exemplary elasticated material 550 which combines at least some of the features of exemplary materials 110 and 510. As can be seen, material 550 includes a first region comprising bonds 562 having first side portions 561. The first region is shown bounded by first lateral portion 581 and first longitudinal portion 583 of the material 550. The bonds 562 may be arranged in bond lines 585, and the first side portions 561, and/or the bond lines 585, may form an angle 571 with respect to elastomeric strands 596 of the material 550. At least some of the bonds 562, for instance such as 562a, 562b, may be disposed on opposite sides of an elastomeric strand 596 and be separated by a longitudinal distance less than the un-tensioned diameter of the elastomeric strand 596. In other words, the bonds 562a, 562b may entrap a portion of the elastomeric strands 596. The material 550 may further comprise a second region comprising bonds 562 having first side portions 563. The second region is shown bounded by second lateral portion 582 and first longitudinal portion 583 of the material 550 The bonds 564 may be arranged in bond lines 587, and the first side portions 563, and/or the bond lines 587, may form an angle 573 with respect to elastomeric strands 596 of the material 550. At least some of the bonds 564, for instance such as 564a, 564b, may be disposed on opposite sides of an elastomeric strand 596 and be separated by a longitudinal distance less than the un-tensioned diameter of the elastomeric strand 596. In other words, the bonds 564a, 564b may entrap a portion of the elastomeric strands 596. It can be seen in FIG. 14 that the angles 571 differ from the angles 573, which are formed by bonds, or more specifically the side portions of bonds or the bond lines formed by the bonds, disposed across the same elastomeric strands 596, which run through both the first and second regions.

Exemplary material 550 further includes third and fourth regions, bounded by the first lateral portion 581 and second longitudinal portion 584 and the second lateral portion 582 and the second longitudinal portion 584, respectively. The third region comprises bonds 566 having first side portions 565. The bonds 566 may be arranged in bond lines 589, and the first side portions 565, and/or the bond lines 589, may form an angle 575 with respect to elastomeric strands 596 of the material 550. At least some of the bonds 566, for instance such as 566a, 566b, may be disposed on opposite sides of an elastomeric strand 596 and be separated by a longitudinal distance less than the un-tensioned diameter of the elastomeric strand 596. In other words, the bonds 566a, 566b may entrap a portion of the elastomeric strands 596. The fourth region comprises bonds 568 having first side portions 567. The bonds 568 may be arranged in bond lines 591, and the first side portions 567, and/or the bond lines 591, may form an angle 577 with respect to elastomeric strands 596 of the material 550. At least some of the bonds 568, for instance such as 568a, 568b, may be disposed on opposite sides of an elastomeric strand 596 and be separated by a longitudinal distance less than the un-tensioned diameter of the elastomeric strand 596. In other words, the bonds 568a, 568b may entrap a portion of the elastomeric strands 596. It can be seen in FIG. 14 that the angles 575 differ from the angles 577, which are formed by bonds, or more specifically the side portions of bonds or the bond lines formed by the bonds, disposed across the same elastomeric strands 596 which run through both the third and fourth regions.

It can be further seen in FIG. 14 that the angles 571 differ from the angles 575, and the angles 573 differ from the angles 577. Accordingly, the material 550 also has regions where the angles that the bonds form, or more specifically the side portions of bonds or the bond lines formed by the bonds, with respect to the elastomeric strands 596 vary across different elastomeric strands 596. In some embodiments, the angles 571 and 577, and the angles 573 and 575, may also differ from each other. In these embodiments, all of the angles of the different regions of the material 550 may differ from each other. Additionally, in some embodiments, the angles 571 and 575, and the angles 573 and 575, may be mirrored about the longitudinal direction 31. That is, the angles 571 and 575, and the angles 573 and 575, may each differ from 90 degrees by the same amount, but one of the angles of the pairs of angles is less than 90 degrees while the other angle of the pairs of angles is greater than 90 degrees. In general, the angles 571, 573, 575, and 575 may have any suitable value, such as those disclosed with respect to angles in the other exemplary elasticated materials of the present disclosure. These different embodiments may allow for an elasticated material with a variety of different stretch properties, which can provide for better fit, function, and aesthetics of absorbent articles or clothing garments using such elasticated materials.

Figure 15:
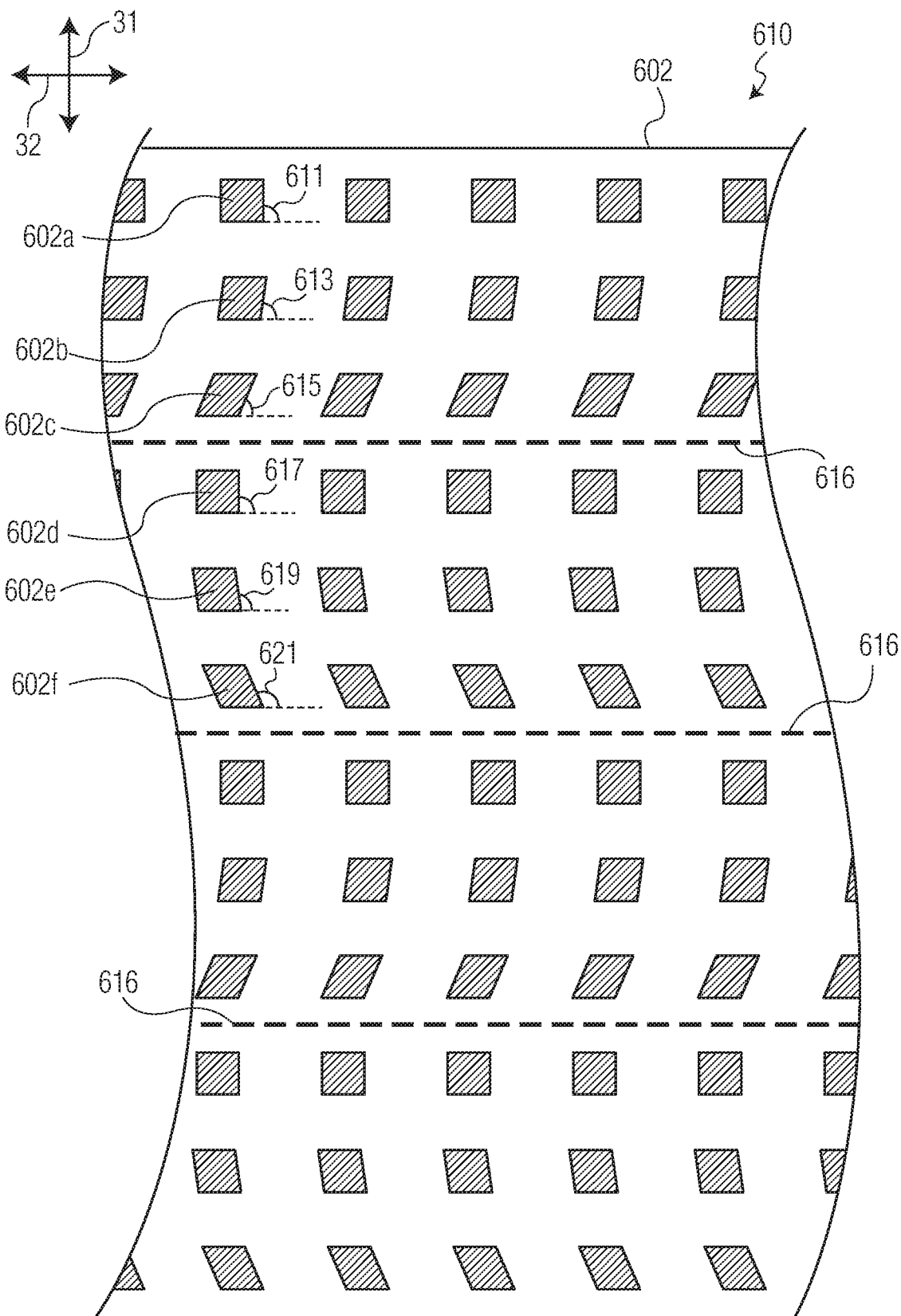
FIG. 15 is a plan view of another exemplary elasticated material that may comprise a portion of a leg cuff of the absorbent article of FIG. 7.

In yet additional embodiments according to the present disclosure, such elasticated materials may have longitudinally adjacent bonds which continuously vary in the angle they form, or more specifically in the angle the side portions of the bonds form, with respect to elastomeric strands of the elasticated material, or lines disposed parallel to the elastomeric strands. In other embodiments, instead of truly continuously varying angles, the angles formed by the bonds may repeat in a pattern every three, four, five, six, seven, eight, nine, or ten, or any other suitable number of bonds. FIG. 15 depicts exemplary elasticated material 610 including top edge 602 and bonds 602a-f. As can be seen, the bonds 602a-f form angles 611, 613, 615, 617, 619, and 621 with respect to the elastomeric strands 616, or lines parallel to the elastomeric strands 616 of the material 610. The angles 611, 613, 615, 617, 619, and 621 form a first unit of a pattern that can be continued longitudinally down the elasticated material 610, and the unit formed by the bonds 602a-f may repeat laterally across the material 610.

In the example of FIG. 15, the each of the angles 611, 613, 615, 617, 619, and 621 may differ from one another, while in other embodiments, the angle 611 and the angle 617 may be the same. Additionally, in some embodiments, the angles 613 and 615 may mirror the angles 619 and 621, respectively about the longitudinal direction. That is, the angle 613 and the angle 619 may each differ from 90 degrees by the same amount, but one of the angles is less than 90 degrees while the other of the angles is greater than 90 degrees. Likewise, the angle 615 and the angle 621 may each differ from 90 degrees by the same amount, but one of the angles is less than 90 degrees while the other of the angles is greater than 90 degrees. In general, the angles 611, 613, 615, 617, 619, and 621 may have any suitable value, such as those disclosed with respect to angles in the other exemplary elasticated materials of the present disclosure. Additionally, it should be understood that the elastomeric strands 616 may be positioned between any of the bonds 602a-f instead of only where shown in FIG. 15. For instance, the elastomeric strands 616 may be positioned between each of the repeating units of bonds instead of within one of the repeating units.

Figure 16:
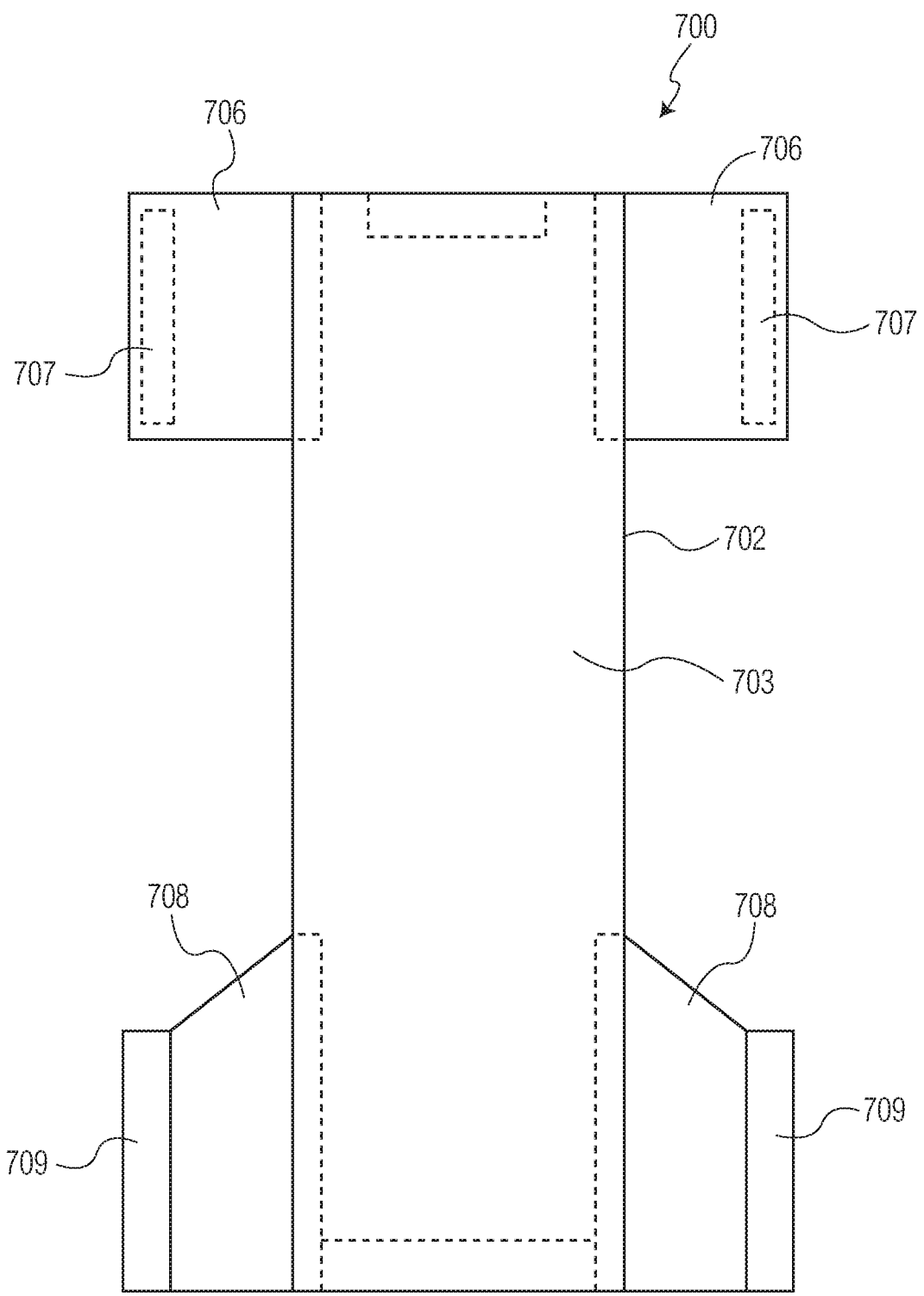
FIG. 16 is a plan view of an exemplary absorbent article including elasticated materials according to aspects of the present disclosure.

In still further embodiments, the elasticated materials of the present disclosure may be useful as side panel materials within absorbent articles. For instance, FIG. 16 depicts exemplary absorbent article 700 including chassis 702 and body facing surface 703. The article 700 may further include front side panels 709 and rear side panels 708. The front side panels 709 may include attachment region 707, while the rear side panels 708 may include attachment region 709. The attachment regions 707, 709 may cooperate with one another to from a secure connection between the front side panels 709 and the rear side panels 709. In such a configuration, the article 700 may be considered to be in a wear configuration.

In some embodiments, it may be beneficial for at least one of the front side panels 709 and/or the rear side panels 708 to have elastic properties, and more particularly elastic properties in the longitudinal direction. For instance, the front and rear side panels 709, 708 may sit on the hips of a wearer of article 700 and having stretchability in the longitudinal direction may provide for an enhanced fit of the article 700 on the wearer.

Figure 17:
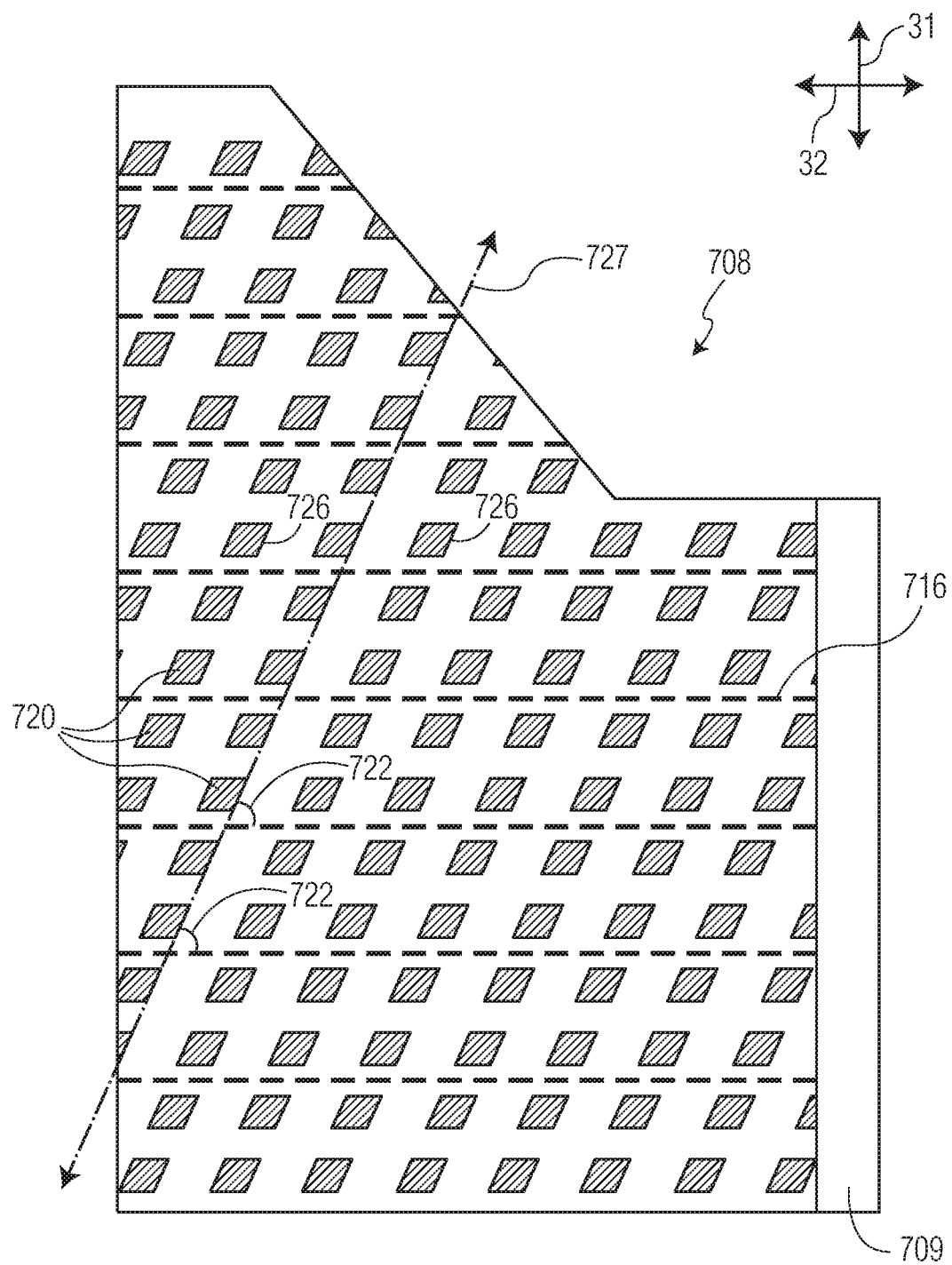
FIG. 17 is a plan view of an exemplary elasticated material that may comprise an ear portion of the absorbent article of FIG. 16.

FIG. 17 further details one of the rear side panels 708, which comprises an elasticated material according to the present disclosure. For example, the rear side panel 708 of FIG. 17 includes bonds 722 having side portions 726. The bonds 720 may be aligned in bond lines 727. Additionally, the side portions, and/or the bond lines, may form an angle 722 with respect to elastomeric strands 716 of the rear side panel 708. The angle 722 may have any suitable value, such as those disclosed with respect to angles in the other exemplary elasticated materials of the present disclosure. Accordingly, as can be seen, the rear side panel 708 of FIG. 17 will elongate in both the lateral direction 32, due to the elastomeric strands 716, and the longitudinal direction 31, due to the elastomeric strands 716 and the specific configuration of the bonds 720 (e.g. where the side portions 726 of the bonds 720, or the bond lines 727, form an angle other than a 90 degree angle with respect to the elastomeric strands 716). In at least some embodiments the rear side panels 708 on opposite sides of the chassis 702 may mirror each other. That is, the angle 720 of the rear side panel 708 on a first side of the chassis 702 may differ from 90 degrees by the same amount as the angle 720 of the rear side panel 708 on a second side of the chassis 702, but one of the angles 720 is less than 90 degrees while the other of the angles 720 is greater than 90.

It should be further understood that contemplated elasticated side panel materials are not limited to the specific configuration of FIG. 17. Rather, elasticated side panel materials contemplated by the present disclosure may include any of the elasticated materials described in the present, for instance as in FIGS. 1-6 and 13-15. Additionally, the front side panels 709 may also be made from elasticated materials of the present disclosure in some contemplated embodiments. The angles formed by the bonds of the different front and rear side panel materials may be the same, or may differ, in some of these contemplated embodiments.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. An elasticated material comprising:
   a first layer of material;
   a second layer of material bonded to the first layer of material by a first pair of bonds comprising a first bond and a second bond and a second pair of bonds comprising a third bond and a fourth bond; and
   a plurality of elastomeric strands extending in a lateral direction and disposed between the first layer of material and the second layer of material and separated in a longitudinal direction,
   wherein the first bond and the second bond are disposed on opposite sides of a first strand of the plurality of elastomeric strands and are separated by a longitudinal distance less than an un-tensioned diameter of the first strand,
   wherein the third bond and the fourth bond are disposed on opposite sides of a second strand of the plurality of elastomeric strands and are separated by a longitudinal distance less than an un-tensioned diameter of the second strand,
   wherein the first bond and the third bond are located on a first side of the first strand and the second strand, respectively, and the second bond and the fourth bond are located on a second side of the first strand and the second strand, respectively,
   wherein the first bond and the third bond comprise first side portions and second side portions,
   wherein the first side portion of the first bond forms a first angle with respect to the first strand of the plurality of elastomeric strands,
   wherein the first side portion of the third bond forms a second angle with respect to the second strand of the plurality of elastomeric strands, and
   wherein the first angle is different than the second angle.

2. The elasticated material of claim 1, further comprising a third pair of bonds comprising a fifth bond and a sixth bond, wherein:
   the fifth bond and the sixth bond are located on opposite sides of a third elastic strand of the plurality of elastic strands and are separated by a longitudinal distance less than an un-tensioned diameter of the third strand,
   wherein the first bond, the third bond, and the fifth bond are located on the first side of the first strand, the second strand, and the third strand, respectively, and the second bond, the fourth bond, and the sixth bond are located on the second side of the first strand, the second strand, and the third strand, respectively,
   the first bond, the third bond, and the fifth bond comprise first side portions and second side portions,
   the first side portion of the fifth bond forms a third angle with respect to the third strand of the plurality of elastomeric strands, and
   the first angle, the second angle, and the third angle are all different.

3. The elasticated material of claim 1, further comprising a third pair of bonds comprising a fifth bond and a sixth bond, wherein:
   the fifth bond and the sixth bond are located on opposite sides of a third elastic strand of the plurality of elastic strands and are separated by a longitudinal distance less than an un-tensioned diameter of the third strand,
   wherein the first bond, the third bond, and the fifth bond are located on the first side of the first strand, the second strand, and the third strand, respectively, and the second bond, the fourth bond, and the sixth bond are located on the second side of the first strand, the second strand, and the third strand, respectively,
   the first bond, the third bond, and the fifth bond comprise first side portions and second side portions,
   the first side portion of the fifth bond forms a third angle with respect to the third strand of the plurality of elastomeric strands, and
   the first angle and the third angle are the same and the second angle is different from the first angle and the third angle.

4. The elasticated material of claim 3, wherein the second strand of the plurality of elastomeric strands is positioned longitudinally between the first strand of the plurality of elastomeric strands and the third strand of the plurality of elastomeric strands.

5. The elasticated material of claim 1, wherein the first angle is less than 90 degrees, and wherein the second angle is greater than 90 degrees.

6. The elasticated material of claim 5, wherein the second angle has a value in degrees that is 180 minus the value of the first angle.

7. The elasticated material of claim 1, wherein the first angle is between about 30 degrees and about 89 degrees, and wherein the second angle is between about 95 degrees and about 145 degrees.

8. The elasticated material of claim 1, wherein the first angle is between about 50 degrees and about 88 degrees, and wherein the second angle is between about 115 degrees and about 135 degrees.

9. The elasticated material of claim 1, wherein the first layer of material and the second layer of material are comprised of separate webs of material.

10. The elasticated material of claim 1, further comprising a third pair of bonds comprising a fifth bond and a sixth bond disposed on opposite sides of the first strand of the plurality of elastomeric strands and separated by a longitudinal distance less than the un-tensioned diameter of the first strand, wherein:
    the first pair of bonds and the third pair of bonds are spaced apart along the first strand of the plurality of elastomeric strands,
    the first bond and the fifth bond are located on the first side of the first strand of the plurality of elastomeric strands and the second bond and the sixth bond are located on the second side of the first strand of the plurality of elastomeric strands, the first bond and the fifth bond comprise first side portions and second side portions, the first side portion of the fifth bond forms a third angle with respect to the first strand of the plurality of elastomeric strands, and the first angle is different than the third angle.

11. The elasticated material of claim 10, further comprising a fourth pair of bonds comprising a seventh bond and an eighth bond disposed on opposite sides of the second strand of the plurality of elastomeric strands and separated by a longitudinal distance less than the un-tensioned diameter of the second strand, wherein:

the second pair of bonds and the fourth pair of bonds are spaced apart along the second strand of the plurality of elastomeric strands, the third bond and the seventh bond are located on the first side of the second strand of the plurality of elastomeric strands and the fourth bond and the eighth bond are located on the second side of the second strand of the plurality of elastomeric strands, the third bond and the seventh bond comprise first side portions and second side portions, the first side portion of the seventh bond forms a fourth angle with respect to the second strand of the plurality of elastomeric strands, the second angle is different than the fourth angle, and the third angle is different than the fourth angle.

12. The elasticated material of claim 11, wherein the third angle is less than 90 degrees, and wherein the fourth angle is greater than 90 degrees.

13. An absorbent article including a front waist region having a front waist edge, a rear waist region having a rear waist edge, a crotch region, a longitudinal axis and a lateral axis, the absorbent article comprising:

a chassis including an absorbent body, the chassis including a body facing surface and a garment facing surface;

a topsheet; and a rear waistband, the rear waistband comprising:

a first plurality of elastomeric strands extending in a lateral direction and disposed between a first layer of material and a second layer of material and separated in a longitudinal direction;

a first bond and a second bond disposed on opposite sides of a first strand of the first plurality of elastomeric strands and separated by a longitudinal distance less than an un-tensioned diameter of the first strand; and a third bond and a fourth bond disposed on opposite sides of a second strand of the first plurality of elastomeric strands and separated by a longitudinal distance less than an un-tensioned diameter of the second strand, wherein the first bond and the third bond are located on a first side of the first strand of the first plurality of elastomeric strands and the second strand of the first plurality of elastomeric strands, respectively, and the second bond and the fourth bond are located on a second side of the first strand of the first plurality of elastomeric strands and the second strand of the first plurality of elastomeric strands, respectively, wherein the first bond and the third bond comprise first side portions and second side portions, wherein the first side portion of the first bond forms a first angle with respect to the first strand of the first plurality of elastomeric strands, wherein the first side portion of the third bond forms a second angle with respect to the second strand of the first plurality of elastomeric strands, and wherein the first angle is different than the second angle.

14. The absorbent article of claim 13, wherein the first layer of material and the second layer of material comprise a first layer of the chassis and a second layer of the chassis, and wherein the first plurality of elastomeric strands are disposed between the first layer of the chassis and a second layer of the chassis within the rear waist region of the absorbent article to form the rear waistband.

15. The absorbent article of claim 13, further comprising a front waistband, the front waistband comprising:

a second plurality of elastomeric strands extending in the lateral direction and disposed between a third layer of material and a fourth layer of material and separated in the longitudinal direction;

a fifth bond and a sixth bond disposed on opposite sides of a first strand of the second plurality of elastomeric strands and separated by a longitudinal distance less than an un-tensioned diameter of the first strand; and a seventh bond and an eighth bond disposed on opposite sides of a second strand of the second plurality of elastomeric strands and separated by a longitudinal distance less than an un-tensioned diameter of the second strand, wherein the fifth bond and the seventh bond are located on a first side of the first strand of the second plurality of elastomeric strands and the second strand of the second plurality of elastomeric strands, respectively, and the sixth bond and the eighth bond are located on a second side of the first strand of the second plurality of elastomeric strands and the second strand of the second plurality of elastomeric strands, respectively, wherein the first bond and the third bond comprise first side portions and second side portions, wherein the first side portion of the first bond forms a first angle with respect to the first strand of the second plurality of elastomeric strands, wherein the first side portion of the third bond forms a second angle with respect to the second strand of the second plurality of elastomeric strands, and wherein the first angle is different than the second angle.

16. The absorbent article of claim 15, wherein the third layer of material and the fourth layer of material comprise a first layer of the chassis and a second layer of the chassis, and wherein the second plurality of elastomeric strands are disposed between the first layer of the chassis and a second layer of the chassis within the front waist region of the absorbent article to form the front waistband.

17. The absorbent article of claim 13, wherein the first angle is less than 90 degrees, and wherein the second angle is greater than 90 degrees.

18. The absorbent article of claim 17, wherein the second angle has a value in degrees that is 180 minus the value of the first angle.

19. The absorbent article of claim 13, wherein a portion of the chassis in the front waist region and a portion of the chassis in the rear waist region are bonded together.

20. An elasticated material comprising:

a first web material;

a second web material bonded to the first web material by a plurality of bonds; and a plurality of elastomeric strands extending in a lateral direction perpendicular to a longitudinal direction and disposed between the first web material and the second web material, wherein the plurality of bonds comprise a first pair of bonds comprising a first bond and a second bond and a second pair of bonds comprising a third bond and a fourth bond, wherein the first bond and the second bond are disposed on opposite sides of a first elastomeric strand of the plurality of elastomeric strands, the first bond and the second bond being separated by a longitudinal distance less than an un-tensioned diameter of the first elastomeric strand of the plurality of elastomeric strands, wherein the third bond and the fourth bond are disposed on opposite sides of a second elastomeric strand of the plurality of elastomeric strands, the third bond and the fourth bond being separated by a longitudinal distance less than an un-tensioned diameter of the second elastomeric strand of the plurality of elastomeric strands, wherein the elasticated material exhibits greater than 1% elongation in the longitudinal direction under an applied force in the longitudinal direction at every angle of rotation of the elasticated material with respect to the longitudinal direction.

* * * * *